United States Patent
Kushnir et al.

(10) Patent No.: US 10,111,979 B2
(45) Date of Patent: *Oct. 30, 2018

(54) WOUND DRESSINGS, METHODS AND APPARATUS FOR MAKING SAME AND STORAGE AND USE THEREOF

(71) Applicant: REDDRESS LTD., Pardes Hana (IL)

(72) Inventors: Alon Kushnir, Herev Le'et (IL); Igal Kushnir, Pardes Hana (IL)

(73) Assignee: RedDress Ltd., Pardes Hana (IL)

( * ) Notice: Subject to any disclaimer, the term of this patent is extended or adjusted under 35 U.S.C. 154(b) by 452 days.

This patent is subject to a terminal disclaimer.

(21) Appl. No.: 14/933,178

(22) Filed: Nov. 5, 2015

(65) Prior Publication Data

US 2016/0256593 A1    Sep. 8, 2016

Related U.S. Application Data

(63) Continuation of application No. 14/247,725, filed on Apr. 8, 2014, now Pat. No. 9,180,142, which is a continuation of application No. 13/145,205, filed as application No. PCT/IL2010/000066 on Jan. 27, 2010, now abandoned.

(60) Provisional application No. 61/147,513, filed on Jan. 27, 2009.

(51) Int. Cl.

| | |
|---|---|
| *A61L 15/00* | (2006.01) |
| *A61L 15/40* | (2006.01) |
| *A61L 15/42* | (2006.01) |
| *A61L 15/44* | (2006.01) |
| *A61K 9/70* | (2006.01) |
| *A61K 35/14* | (2015.01) |
| *A61J 1/16* | (2006.01) |

(52) U.S. Cl.
CPC .............. *A61L 15/40* (2013.01); *A61J 1/16* (2013.01); *A61K 9/7007* (2013.01); *A61K 35/14* (2013.01); *A61L 15/42* (2013.01); *A61L 15/44* (2013.01); *A61L 2300/102* (2013.01); *A61L 2300/216* (2013.01); *A61L 2300/418* (2013.01); *A61L 2300/42* (2013.01); *A61L 2300/45* (2013.01); *A61L 2400/04* (2013.01)

(58) Field of Classification Search
None
See application file for complete search history.

(56) References Cited

U.S. PATENT DOCUMENTS

| | | |
|---|---|---|
| 3,723,244 A | 3/1973 | Breillat, Jr. et al. |
| 4,035,483 A | 7/1977 | Bunyan |
| 4,347,841 A | 9/1982 | Benyo et al. |
| 5,610,148 A | 3/1997 | Brown |
| 5,629,287 A | 5/1997 | Brown et al. |
| 6,521,265 B1 | 2/2003 | Patterson |
| 2002/0146446 A1 | 10/2002 | Solomon |
| 2003/0077272 A1 | 4/2003 | Pathak |
| 2004/0124564 A1 | 7/2004 | Noorjahan et al. |
| 2004/0147024 A1 | 7/2004 | Crowe et al. |
| 2004/0171145 A1 | 9/2004 | Jorcano Noval et al. |
| 2007/0077610 A1 | 5/2007 | Ghai et al. |
| 2007/0275461 A1 | 11/2007 | Jorcano Noval et al. |
| 2008/0098329 A1 | 4/2008 | Csore et al. |
| 2009/0011043 A1 | 1/2009 | Xie |
| 2011/0318404 A1 | 12/2011 | Kushnir et al. |

FOREIGN PATENT DOCUMENTS

| | | |
|---|---|---|
| EP | 0265906 A2 | 5/1988 |
| GB | 891 963 A | 3/1962 |
| JP | 5234916 | 8/1976 |
| JP | 1977034916 | 3/1977 |
| JP | 02-291866 | 12/1990 |
| JP | 09269324 | 10/1997 |
| JP | 2004339496 | 2/2004 |
| JP | 2004530448 | 10/2004 |
| WO | 98/12274 A1 | 3/1998 |
| WO | 01/21195 A1 | 3/2001 |
| WO | 0164148 A1 | 9/2001 |
| WO | 2004108146 A1 | 12/2004 |
| WO | 2008109160 A2 | 9/2008 |

OTHER PUBLICATIONS

Davis, "The Blood-Clot Dressing in Frontal Sinus Surgery", Wiley Online Library, 1919, 29(1), pp. 5-8.
Henderson, et al. "The effects of autologous platelet gel on wound healing," ENT-Ear, Nose & Throat Journal, (2003) pp. 597-602.
Khalafi, et al., "Topical application of autologous blood products during surgical closure following a coronary artery bypass graft," European Journal of Cardio-thoracic Surgery, (2008), vol. 34, pp. 360-364.
Moorhead, et al., "Human Red Cell Concentrate for Surgical Dressings," American Journal of Surgery, (1943), vol. 59, No. 1, pp. 104-105.
Travis, "Building Better Bandages," The Weekly Newsmagazine of Science, (1999), vol. 155, No. 25, five (5) pages.
International Search Report, International Application No. PCT/IL2010/000066, dated Nov. 18, 2010, two (2) pages.
Githens et al., "The prevention of blood clotting by Dakin's sodium hypochlorite solution", Prevention of Blood Clotting, 184 (1362), Expo Biol Med (Maywood) May 1918.
Office Action issued in U.S. Appl. No. 13/145,205 dated Feb. 24, 2014.
Office Action issued in U.S. Appl. No. 13/145,205 dated Oct. 9, 2011.
Office Action issued in U.S. Appl. No. 13/145,205 dated Mar. 28, 2013.
Office Action issued in U.S. Appl. No. 13/145,205 dated Feb. 21, 2013.

*Primary Examiner* — Hasan S Ahmed
(74) *Attorney, Agent, or Firm* — Greenberg Traurig, LLP

(57) ABSTRACT

Provided is a wound dressing prepared from whole blood that is clotted ex vivo to form a sheet of clotted blood that is applied onto the skin over a sight of skin injury.

7 Claims, 16 Drawing Sheets

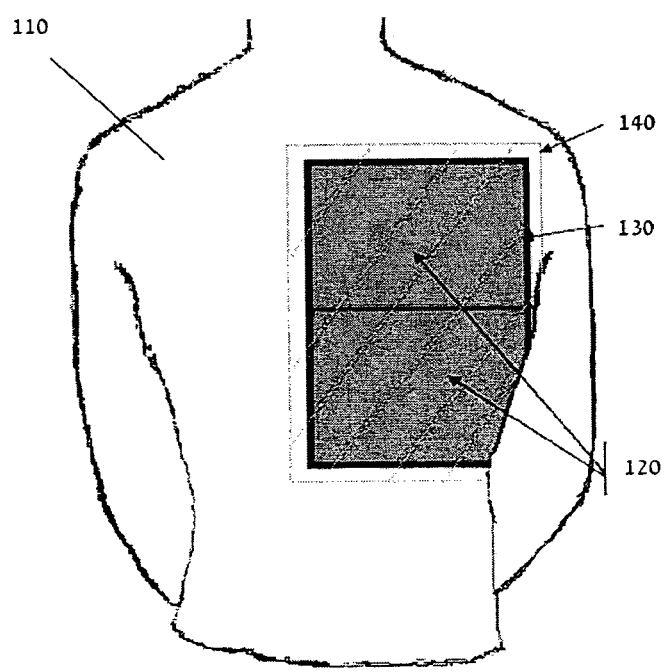

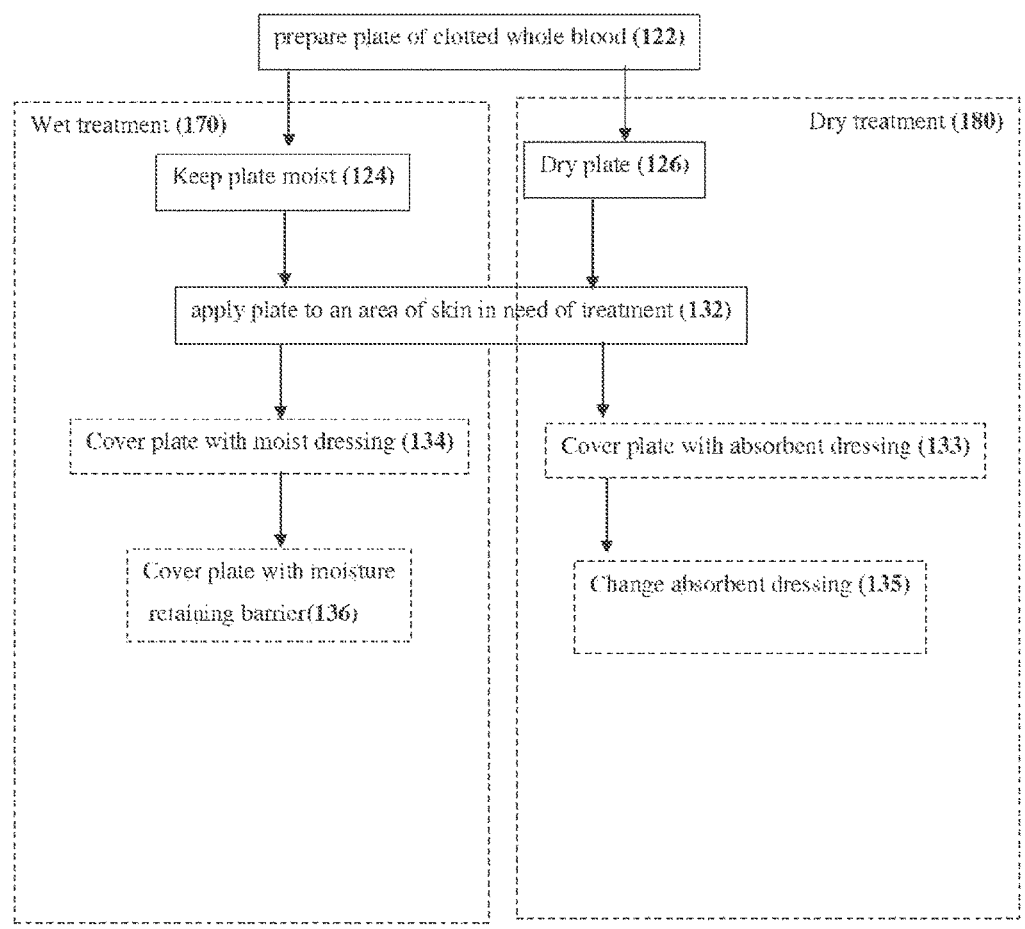

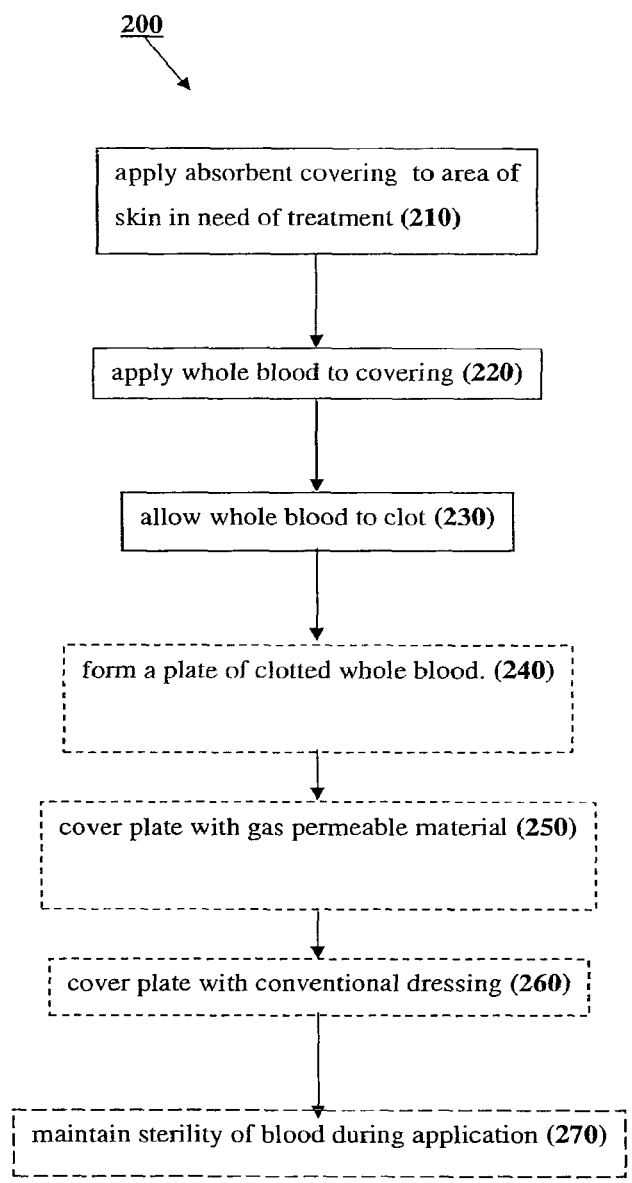

Fig. 6A        600
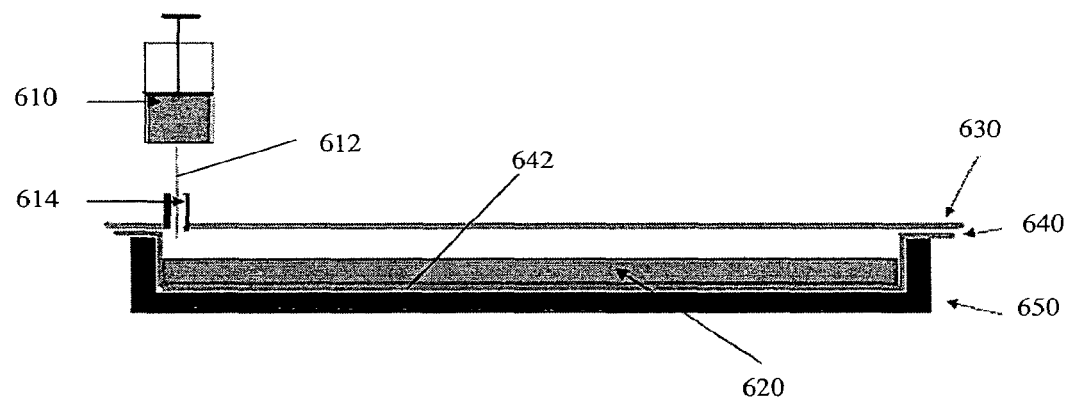
Fig. 6B        601
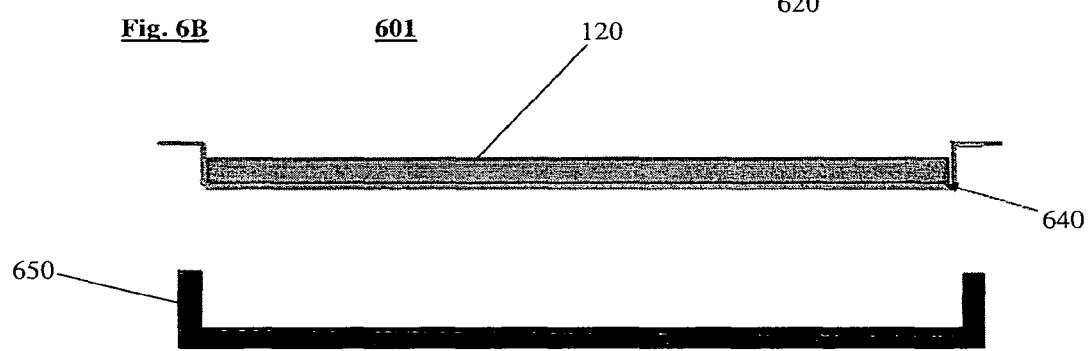

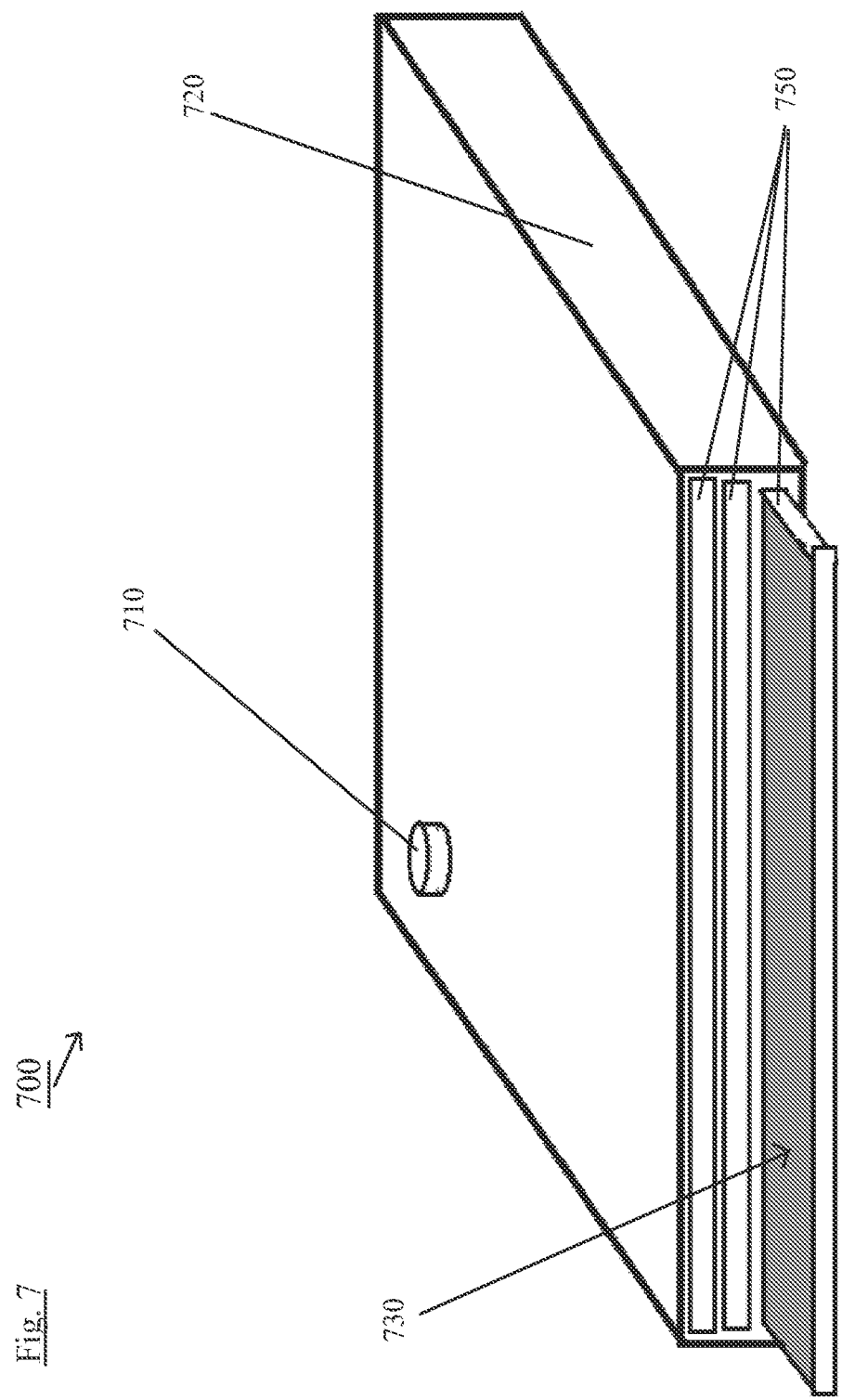

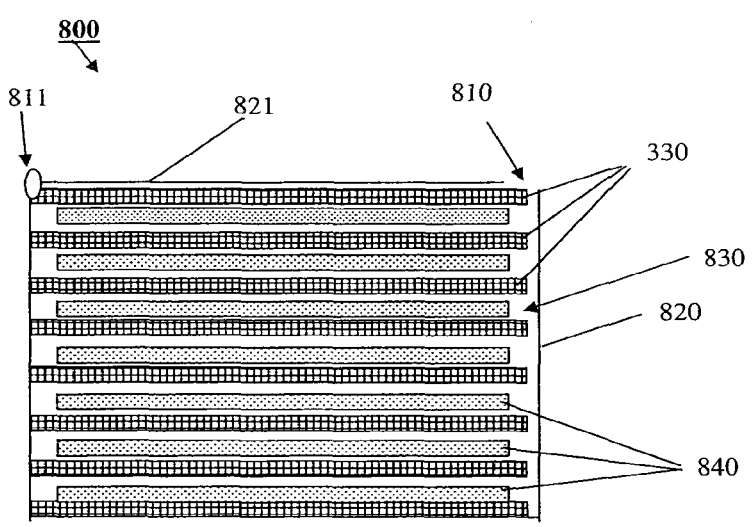

Fig. 10     1000
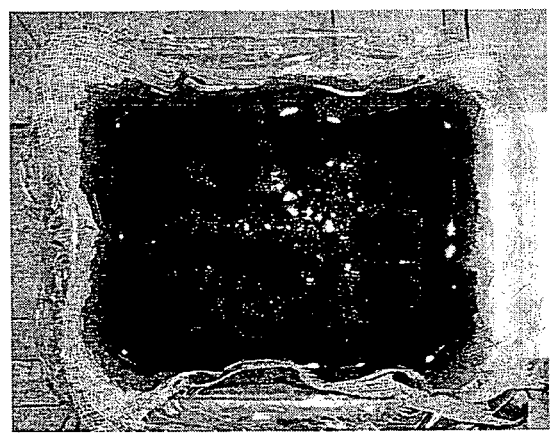
Fig. 11     1100

Fig. 12    1200
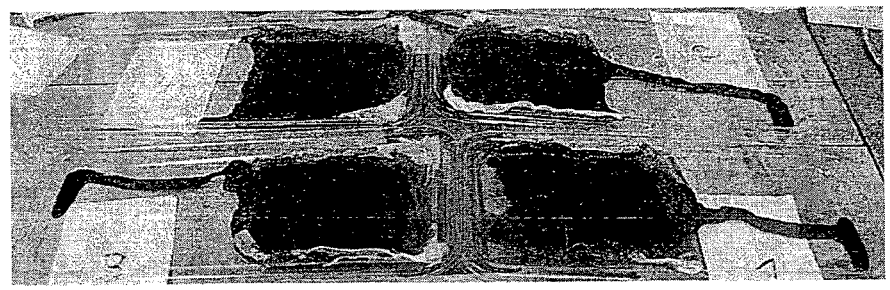
Fig. 13    1300
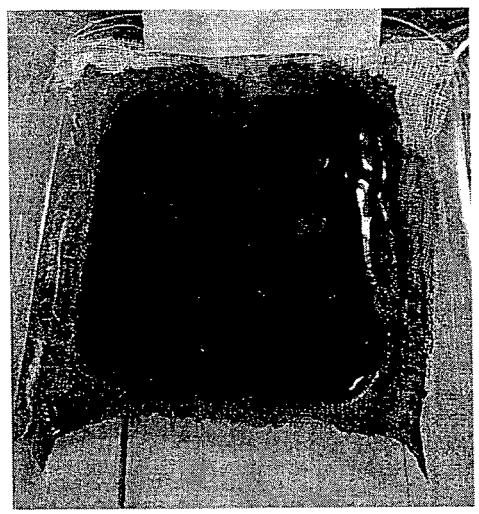
Fig. 14    1400

WOUND DRESSINGS, METHODS AND APPARATUS FOR MAKING SAME AND STORAGE AND USE THEREOF

RELATED APPLICATIONS

This application is a continuation of U.S. application Ser. No. 14/247,725, filed Apr. 8, 2014, which is a continuation of U.S. application Ser. No. 13/145,205, with a 371 (c) filing date of Sep. 14, 2011, which is a National Phase Application filed under 35 U.S.C. § 371 as a national stage of PCT/IL2010/000066, filed on Jan. 27, 2010, an application claiming the benefit under 35 U.S.C. § 119(e) of U.S. Provisional Application No. 61/147,513, filed on Jan. 27, 2009, the content of each of which is hereby incorporated by reference in its entirety.

FIELD OF THE INVENTION

This invention relates to wound dressings, as well as to methods and apparatus for producing and/or using the dressings, storage of the dressings and use of the dressings.

BACKGROUND OF THE INVENTION

The skin is the largest organ of the mammalian body and serves several critical functions. In some cases, the skin is disrupted by trauma (e.g. laceration, abrasion, burns or puncture) or by ulceration (e.g. diabetic foot ulcers). Disruptions in the skin which do not heal, or spontaneously recur, are known as chronic wounds (Fowler (1990) in Chronic wounds: an overview. In: Krasner D, editor. Chronic wound care: a clinical source book for healthcare professionals. King of Prussia, Pa.: Health Management Publications, Inc.; pp. 12-8 and Singh et al. (2004) Asian J Surg 27:326-32).

Approximately 1% to 2% of individuals will be affected by leg ulceration during their lifetime, and this figure will likely increase as the population ages (Rees and Hirshberg (1999). Adv Wound Care 1999; 12:4-7 and Callam M. (1992) Phlebology 7:S6-S12). Global wound care expenses reaches up to $13 to $15 billion annually (Walmsley (2002) In: Clinica reports. London: PJB Publications, Ltd.).

Patient groups suffering chronic wounds include, but are not limited to, diabetic patients, geriatric patients and patients with circulatory problems. Also, chronic wounds can appear as a result of acute trauma or as a post surgery symptom.

Chronic wounds may vary in size, depth and stage of healing. Wounds can contain necrotic tissue, infection, scabs, or exudates (purulent, cerotic).

Chronic wounds can be classified by their cause such as pressure, diabetic, ischemic, venous, and tear and/or by the nature of the wound itself such as its depth and/or stage of healing and/or discharge and/or infections. Burns are another wound type which is difficult to treat.

Conventional burn treatment typically relies upon a topical antibiotic cream (e.g. Silver sulfadiazine) followed by a non-stick dressing and gauze. Use of biologic dressings based upon cultured cell grafts and/or fractionated blood products has also been suggested. According to different burn management strategies, frequency of dressing changes can vary from twice per day to about once per week.

A number of non conventional burn treatment strategies have been proposed. A non-exhaustive overview of some of the art follows.

WO/2001/021195 describes a dressing including preformed fibrin that functions as a non-adhesive covering of a burned skin surface as well as functioning as a delivery vehicle for pharmaceutical compounds that are entrapped within the fibrin clot.

J. Travis (Science News Online 155 (25); Jun. 19, 1999) describes fibrin bandages produced by Martin MacPhee at the American Red Cross' Holland Laboratory in Rockville, Md. The bandages employ a cloth made of biodegradable material saturated with thrombin, fibrinogen, and factor 13 purified from human blood. The bandages are brittle until they get wet, and then they become flexible.

US 2002/0146446 describes a surgical-medical dressing which uses a sandwich of two extracellular matrices grown on a composite composed of gelatin-fibronectin-heparan sulfate. The culture medium used to grow the two cell types (dermal fibroblasts and dermal microvascular endothelial cells forming the second extracellular matrix) is the conditioned medium (CM) obtained from human umbilical endothelial cells used to form the first extracellular matrix. All cells in tissue culture are detached leaving their secreted acellular matrix behind and intact. This CM can also neutralize the enzyme DISPASE commercially used to detach cultured epithelial sheets ("Cultured epithelial autografts" (CEAs)) from the matrix on which the human epidermal cells, forming the sheets are grown. CEAs are clinically used in wound and burn management Henderson L. et al, discloses the healing of superficial skin burns by a autologous platelet gel dressing. (Ear, Nose & Throat Journal, 2003).

U.S. Pat. No. 3,723,244 describers a method of producing fibrin in sheet form by centrifuging an aqueous dispersion of fibrin wherein monomeric fibrin molecules are combined by polymerization to form strands of fibrin. The centrifuging step is conducted in a vessel having a wall for interception of particles undergoing centrifugal acceleration therein and at a speed pelletizing on said wall the strands of fibrin resulting from polymerization, so that the pelletized strands interlock to form a sheet which is recovered from the wall. The aqueous dispersion can be blood plasma and the resultant fibrin sheets are described as useful as a dressing for burns.

U.S. Pat. No. 6,521,265 describes a method of promoting healing of a bleeding wound including mixing a substantially anhydrous compound of a salt ferrate, which hydrates in the presence of water to produce $Fe^{+++}$ and oxygen, combined with an insoluble cation exchange material, with a quantity of an aqueous media such as whole blood taken directly from the wound with deionized water; aqueous sodium chloride; aqueous dissolved gelatin; aqueous carboxy methacel; and aqueous carbohydrate solution to form a spreadable paste. The paste is applied to the wound within a short working time to promote blood clotting. According to the description, the presence of oxygen, substantially reduces the level of bacteria, virus and fungus at the wound as a protective coating forms over the wound.

U.S. Pat. No. 4,347,841 describes biological dressing for burn wounds formed by removing free hemoglobin from a red blood cell concentrate which is subjected to hemolysis. The dressing contains the stroma, subcellular elements and precipitated protein from the human red blood corpuscle concentrate freed from the hemoglobin and can be used in a pulverulant or layer form with, if desired, an appropriate support.

US 2007/0275461 and US 2004/0171145 describe artificial dermis obtained from plasma with platelets and human fibroblasts. The plasma with platelets is obtained from fractionating whole blood from the patient by light centrifugation, and the human fibroblasts are obtained from a skin biopsy. Clotting is obtained by adding calcium. The artificial dermis is described as providing for rapid growth of keratinocytes seeded on its surface to build an artificial skin which can easily be transplanted. Large areas of artificial dermis are described as being obtained from a small skin biopsy and minimal quantities of plasma with platelets. The artificial skin is described as useful to treat major burns, chronic skin ulcers, or be used with genetically altered cells as a vehicle for gene therapy.

US 2004/0124564 describes a process for the preparation of a chemically modified fibrin-fibrillar protein (FFP) composite sheet for medical application and the FFP composite prepared thereby. According to the description, the FFP sheet finds potential use as a dressing aid in the treatment of various external wounds including burn wounds.

Use of purified or fractionated blood components in other medical contexts is also described. A non-exhaustive overview of some of the art follows.

Khalafi et al. (*Eur J Cardiothorac Surg* 2008; 34:360-364.) describes application of platelet rich and platelet poor plasma to significantly reduce occurrences of chest wound infection, chest drainage, and leg wound drainage in coronary artery bypass grafts.

Medtronic, Inc., Minneapolis, MV; USA produces devices for processing autologous blood to concentrate platelet-rich plasma into an autologous platelet gel for use in surgery for improving tissue healing.

Some commercially available wound care products use blood fractions and/or factors isolated from blood.

For example, a variety of growth factors have been found to play a role in the wound healing process, including platelet derived growth factor (PDGF), epidermal growth factor, fibroblast growth factors, transforming growth factors, and insulin-like growth factor. Various wound healing technologies based on fractionated blood or blood derived growth factors are commercially available.

One commercially available technology employs recombinant DNA techniques to create purified growth factors. REGANEX™ Gel (manufactured by Systagenix Wound Management) is a topical gel, containing the active ingredient becaplermin with an activity similar to that of human platelet derived growth factor (PDGF). This recombinant growth factor is produced by recombinant DNA technology by insertion of the gene for the B chain of platelet-derived growth factor (PDGF) into *Saccharomyces cerevisiae*.

Another commercially available technology employs platelet rich plasma (PRP). PRP is isolated from whole blood by centrifugation. Autologous PRP contains a mixture of activated growth factors cytokines and chemokines, with reduced potential for immune response. Exposure of PRP to a solution of thrombin and calcium chloride results in the polymerization of fibrin from fibrinogen, creating a platelet gel which can then be applied to wounds. The PRP provides the wound with growth factors, chemokines and cytokines that promote angiogenesis and regulate cell growth and formation of new tissue. AutoloGel™ (manufactured by Cytomedix, Inc.) and SafeBlood® (manufactured by SafeBlood Technologies) are two autologous blood-derived products that can be prepared at the bedside for immediate application. Both AutoloGel™ and SafeBlood® have been specifically marketed for wound healing.

Another commercially available technology employs fibrin glues or sealants with hemostasis and gluing properties which enhance wound healing. Commercial fibrin glues are created from pooled homologous human donors. TISSEEL™ (manufactured by Baxter) is an example of commercially available fibrin sealant. The action of this product allegedly simulates key features of the physiological process of wound closure. The product contains a highly concentrated fibrinogen aprotinin solution, which among other ingredients contains Factor XIII, and a solution of thrombin and calcium chloride are applied to the wound area, where the mixture coagulates. The presence of Factor XIII causes the fibrin to crosslink, which gives the coagulum additional resilience.

SUMMARY OF THE INVENTION

A broad aspect of the invention relates to treatment of skin injuries using clotted blood. The clotted blood is formed so it can be applied onto a skin injury.

The term "whole blood" should be understood as referring to (i) blood taken from venous or arterial circulation; (ii) (ii) blood that has not been modified except for the addition of an anticoagulant or other chemical or biological substances or removal of one or more blood components (e.g. a portion of the plasma), where such modification does not affect its overall physical or chemical characteristics; or (iii) blood containing all its components, such as red and white blood cells, platelets and more, particularly all components required for clot formation. It should be noted that the term "whole blood" does not necessarily mean that the blood used as a source for the clotted blood is identical to the blood withdrawn from an individual. At times, the withdrawn blood may be subject to procedures such as dialysis, passage through a column, etc., in order to remove certain, e.g. undesired, component before being used in therapy of skin injuries according to the invention (an example is the removal of certain immunogenic or anti-sera components in the case of the use of a non-autologous blood). Also, according to some exemplary embodiments of the invention the whole blood is supplemented with one or more additives. Additives include, but are not limited to coagulation influencing additives, physical property changing additives and medically active additives.

Skin injuries treatable in accordance with the invention include all kinds of injuries of the skin where skin is missing or where the therapy targets, among others, skin re-growth. These include both non-bleeding wounds (e.g. burns and ulcers) and bleeding wounds (e.g. abrasions).

Coagulation influencing additives include, but are not limited to anticoagulants, anti-anticoagulants and/or coagulation accelerators (such as negatively-charged phospholipids (PL) and surface contact agents as Kaoline). In order to avoid uncontrolled blood clotting, one or more anticoagulants (e.g. EDTA) may be added to the blood immediately upon withdrawal from an individual. Anticoagulants are in fact typically included in test tubes or other containers where the blood is collected. Also, blood stored in a blood bank typically includes one or more anticoagulants. According to some exemplary embodiments of the invention in order to counteract the anti-coagulant in the whole blood preparation, an anti-anticoagulant is added to permit the blood to clot. For example, $Ca^{2+}$ ions can be used to counteract the activity of EDTA. These ions can be added as a solution of a soluble calcium salt. Since the type and amount of anticoagulant added to a unit of whole blood are typically known, it is possible to select an appropriate anti-anticoagulant and calculate an appropriate amount to use.

Physical property changing additives include, but are not limited to, diluents (e.g. saline solutions), hardeners (e.g. minerals), plasticizers and elasticizers.

Medically active additives include but are not limited to antibiotics, antiseptics, analgesics, growth factors, cytokines, enzymes, hormones, cells, anti-inflammatory agents and many others as may be envisaged by one of ordinary skill in the art of wound care.

Use of medically active and physical property changing additives is described in US 2004/0147024, U.S. Pat. No. 5,610,148 and U.S. Pat. No. 5,629,287 the relevant content of which being incorporated herein by reference.

Some exemplary embodiments of dressing as disclosed herein are based upon the realization that a blood clot naturally contains the physical, chemical and functional properties which make it an effective dressing to cover the wound and promote healing. Without wishing to be bound by theory, it is believed that clotted whole blood must necessarily address all basic requirements of a wound dressing. Optionally, by using an autologous blood clot (a clot from whole blood extracted from the patient) any potential for an immune response is greatly reduced. Optionally, when using a homologous blood clot (namely a clot from whole blood extracted from a different individual, e.g. obtained from a blood bank), the potential for immune response can be reduced by serological typing.

An aspect of some embodiments of the invention relates to formation of a layer or sheet of clotted whole blood on a support structure. According to some exemplary embodiments of the invention the support structure is embedded within the clotted whole blood. Alternatively or additionally, the support structure is external to the clot. According to some exemplary embodiments of the invention the support structure aids in transfer of the clotted whole blood from one location to another and/or contributes to a change in contraction behavior during clotting and/or contributes to a change in physical properties of the resultant whole blood clot (e.g. increased strength). An example of a support structure is a pad of a fibrous material such as gauze.

An aspect of some embodiments of the invention relates to concurrent formation of a plurality of sterile whole blood clots from a source of whole blood. According to some exemplary embodiments of the invention the clots are formed in sheets of a desired thickness. Optionally, the sheets in the plurality have a common thickness. Optionally, the sheets are formed on a support structure.

An aspect of some embodiments of the invention relates to a sterile sheet of clotted whole blood including an anticoagulant and sufficient anti-anticoagulant to permit clotting. According to some exemplary embodiments of the invention the sterile sheet of clotted blood is provided in a package or wrapper which maintains sterility during storage and/or transit. Also the blood clot is typically formed as a sheet, the invention is not limited to blood clots formed into such a specific form.

An aspect of some embodiments of the invention relates to application of clotted whole blood to a skin surface of a subject. According to various exemplary embodiments of the invention the clotted whole blood can be applied as part of a wet dressing or a dry dressing. According to some exemplary embodiments of the invention the skin surface includes a wound (e.g. ulcer or laceration) and/or a burned skin surface.

Optionally, the clotted whole blood is applied with an internal and/or an external support as described hereinabove and hereinbelow. According to some exemplary embodiments of the invention the clotted whole blood is covered with a conventional dressing. The term "conventional dressing" as used in this specification and the accompanying claims refers to a covering including one or more layers each independently selected from a non adhesive layer, an absorbent layer (e.g. gauze and/or non woven fabric or similar mesh) and an adhesive layer (e.g. tape).

An aspect of some embodiments of the invention relates to a bank of dressings prepared from units of clotted whole blood. According to some exemplary embodiments of the invention the dressings are catalogued by unique identifiers corresponding to the units. Optionally, the unique identifiers are used to match a subject to one or more specific biological dressings.

Optionally, matching information is provided as machine readable data associated with said unique identifier in a look up table in a memory of a computer. Machine readable data includes, but is not limited to, data related to blood type, cross-match data, HLA haplotype data and other genetic data. Alternatively or additionally, matching information is provided as an aliquot of un-clotted blood reserved from each of said units of whole blood from which each of said plates in said plurality was prepared, each aliquot associated cataloged by said unique identifier. "Blood type" as used herein refers to any antigen and/or antibody characterization and is not limited to A; B; AB; O and $Rh^{+/-}$.

An aspect of some embodiments of the invention relates to spreading an amount, e.g. a unit of whole blood obtained from a donor or blood bank over an area, e.g. 50-10,000 $cm^2$, and allowing the blood to form a clot. According to some exemplary embodiments of the invention sterility of the blood is maintained during clotting. As can readily be understood, the area measures noted above are exemplary and they may be smaller or larger. There may, at times, be a tradeoff between strength of the resultant blood clot sheet and area, with larger areas producing weaker clots. According to some exemplary embodiments of the invention a support layer contributes strength that permits spreading of the blood over a larger area. In general, the thickness of blood is reduced during clot formation by weeping or sweating of plasma from the clot during and/or after formation. For example, a 3 mm layer of whole blood produces a clot with a thickness of about 1.2 mm after 1 day in vitro. According to some exemplary embodiments of the invention a coagulation initiator is added prior to spreading. Optionally, the coagulation initiator is selected to neutralize activity of an anticoagulant in the blood.

An aspect of some embodiments of the invention relates to use of unfractionated whole blood in manufacture of a wound blood dressing.

An aspect of some embodiments of the invention relates to application of whole blood to an area of skin in need of treatment to form a blood clot thereon. According to some exemplary embodiments of the invention the area is covered by an absorbent layer. Optionally, the absorbent layer includes a mesh such as gauze and/or non-woven fabric. Optionally, the clot is covered after formation. According to some exemplary embodiments of the invention burned skin is treated. Optionally, sterility of the blood is maintained during application.

An aspect of some embodiments of the invention relates to cutting slices or sheets of clotted whole blood from a block of clotted whole blood. The term "block" as used in this specification and the accompanying claims should be interpreted broadly so that it includes all three dimensional shapes.

As used in this specification and the accompanying claims, the adjective "removable" indicates the described object has been engineered to allow removal by an average user without undue effort. Removable includes both items which are removed without tools, and those that require use of a tool (e.g. scissors, knife or opener). In some exemplary embodiments of the invention, tools for removal are provided with their matching removable parts in the manner of a sardine can with an attached "key".

According to an embodiment of the invention there is provided a device for clotting whole blood and forming it into a clot for use in treatment of a skin injury. The device has a blood receptacle for receive the blood, the receptacle being shaped in a manner so as to impart a desired final shape, e.g. planar, on the formed blood clot.

According to some exemplary embodiments of the invention a device for clotting whole blood ex-vivo is provided, the device comprising: (a) an inlet including a channel of fluid communication to an interior of the device; (b) a sample receptacle adapted to spread a sample provided therein to produce a uniform layer; and (c) at least one support structure deployed in the receptacle so that the uniform layer forms on the structure. It optionally includes, also (d) a removable cover covering the receptacle and adapted to maintain sterility of the layer.

Optionally, the support structure includes an external layer.

Optionally, the support structure is adapted to become embedded in the layer.

Optionally, the layer is constructed of a material which adheres to a blood clot formed thereupon.

Optionally, the support structure includes at least one material selected from the group consisting of nylon, polyurethane, cotton, cellulose, a silicon and rubber.

Optionally, the receptacle is constructed of at least one material selected from the group consisting of glass, cellulose, polystyrene, polyurethane, polyvinylchloride, polycarbonate and a rubber.

Optionally, the receptacle contains a sufficient amount of an anti-anti-coagulant to cause coagulation of blood including the sample.

Optionally, the interior of the device is under vacuum pressure.

According to some exemplary embodiments of the invention there is provided a device for clotting whole blood ex-vivo, the device comprising: (a) at least one inlet including a channel of fluid communication to an interior of the device; (b) a plurality of sample receptacles interconnected to allow concurrent inflow from a common source, each of the receptacles adapted to spread a sample provided therein to produce a uniform layer, e.g. a sheet; (c) a sterility guard adapted to maintain sterility of the layer in each of the receptacles.

Optionally, the device includes a support structure deployed in each of the receptacles so that the layer forms on the support structure.

Optionally, the support structure includes an external layer constructed of a material which adheres to a blood clot formed thereupon.

Optionally, the support structure includes a mesh embedded in the layer.

Optionally, the interconnection is in at least one configuration selected from the group consisting of in parallel and in series.

Optionally, the receptacles are arranged in a stack.

Optionally, removal of one of the receptacles does not affect sterility of the layer in any other receptacle.

Optionally, the sterility guard includes a cover associated with at least some of the receptacles.

Optionally, at least some of the receptacles serve as the sterility guard for another of the receptacles.

Optionally, the device further includes an outlet valve providing fluid communication between the interior of the device and an ambient environment.

Optionally, the interior of the device is provided under vacuum.

Optionally, each of the receptacles contains a sufficient amount of an anti-anti-coagulant to cause coagulation of blood including the sample.

Provided by the invention is also a kit or assembly comprising one or more of the components needed in order to prepare a blood clot-based dressing in accordance with the invention. Such components comprise one or more of the following: one or more blood withdrawal devices; one or more blood collection receptacles; one or more plates, trays or other suitable receptacles for receiving the blood and forming a clot thereon; one or more support matrices for the formed blood clot; an anticoagulant optionally already included in the in the blood withdrawal or blood collection devices; an anticoagulant inhibitor (also referred to in this specification as anti-anticoagulant) for inducing clot formation. The kit or assembly optionally comprises also instructions for use in accordance with the invention.

According to some exemplary embodiments of the invention there is provided a kit or assembly, comprising: (a) a sterile tray or plate intended for receiving whole blood; (b) an anticoagulant material dispersed throughout the plate or included in a container and intended for adding to the tray or plate before or after blood is introduced therein; and (c) an anticoagulant inhibitor to permit formation of the clot despite presence of the anticoagulant. Optionally, the anticoagulant includes at least one substance selected from the group consisting of EDTA (ethylenediaminetetraacetic acid), EGTA (ethylene glycol tetraacetic acid), a citrate, Heparin and oxalate.

Optionally, the anticoagulant inhibitor is selected from $Ca^{2+}$, $Mg^{2+}$, Kaolin, negatively charged phospholipid (PL) and protamine sulfate.

Optionally, the kit or assembly is provided at ambient temperature.

Optionally, the kit or assembly is provided under refrigeration.

According to some exemplary embodiments of the invention there is provided a method of treatment, comprising: (a) preparing a clotted whole blood sheet; and (b) applying the sheet to an area of skin of a subject in need thereof.

Optionally, the method includes adhering a support matrix onto the clotted blood sheet.

Optionally, the method includes embedding a mesh within the clotted blood sheet.

Optionally, the matrix has a functionally significant permeability to at least one item selected from the group consisting of a gas and a liquid.

Optionally, the matrix is constructed of at least one material selected from the group consisting of nylon, polyurethane, silicon and rubber.

Optionally, the sheet is at least 1, or at least 2 or at least 3 mm thick.

Optionally, the method includes covering the sheet with a conventional dressing.

Optionally, the method includes maintaining sterility of the clotted blood sheet from its formation until use.

According to some exemplary embodiments of the invention there is provided a bank of biological dressings, the bank, comprising: (a) a plurality of sterile sheets of clotted whole blood, each of the plates cataloged by a unique identifier indicating a unit of whole blood from which the sheet was derived; (b) cross compatibility information for each of the units of whole blood; and (c) a refrigeration unit for cold storage of the plurality of plates.

Optionally, the cross compatibility information is provided as machine readable data associated with the unique identifier in a look up table in a memory of a computer.

Optionally, the cross compatibility information is provided as an aliquot of un-clotted blood reserved from each of the units of whole blood from which each of the plates in the plurality was prepared, each aliquot associated cataloged by the unique identifier.

Optionally, at least some of the sterile plates of clotted whole blood comprise an external support structure in contact with the plate.

Optionally, at least some of the sterile plates of clotted whole blood comprise a mesh embedded in the plate.

According to some exemplary embodiments of the invention there is provided a method of producing a biological dressing, comprising: a) spreading a unit of whole blood to cover an area while maintaining sterility; and b) allowing the blood to form a clot, typically in the form of a sheet.

Optionally, the method comprises adding a coagulation initiator prior to the spreading.

Optionally, the coagulation initiator is selected to neutralize an activity of an anticoagulant in the unit.

Optionally, the spreading occurs in a receptacle overlaid with a layer which prevents contact between the whole blood and the receptacle.

Optionally, the spreading is on a mesh which becomes embedded in the clot.

Optionally, the matrix adheres to the clot and contributes to a transferability thereof.

Optionally, the matrix is constructed of at least one material selected from the group consisting of nylon, a polyurethane, a woven fabric, a non-woven fabric, silicon, rubber and organosilicone.

Some exemplary embodiments of the invention relate to use of unfractionated whole blood in the manufacture and/or preparation of a wound dressing.

According to some exemplary embodiments of the invention there is provided a method of treatment comprising: (a) providing an absorbent matrix adapted for covering an area of skin of a subject in need of treatment; (b) permitting an amount of whole blood to clot on said matrix to form a sheet of clotted whole blood thereon; and (c) applying the clotted blood-containing dressing on a skin injury.

Optionally, the blood includes autologous blood from the subject.

Optionally, the matrix includes a mesh.

Optionally, the mesh includes gauze.

Optionally, the method includes covering the sheet with a gas permeable material.

Optionally, the area of skin includes a non-bleeding wound (e.g. burned area or ulcer).

Optionally, the method includes covering the sheet with a conventional dressing.

Optionally, the method includes maintaining sterility of the blood during the application.

According to some exemplary embodiments of the invention there is provided a method for preparing plates of clotted whole blood, the method comprising: (a) providing a block of clotted whole blood in a cutting apparatus; (b) advancing the block incrementally; (c) cutting a slice from the block; and (d) alternately repeating (b) and (c).

In some exemplary embodiments of the invention, there is provided a method of preparing a wound dressing including: (a) collecting a volume of blood; and (b) clotting the blood ex vivo to form a clot.

Optionally, the method includes cutting a portion of the clot to dimensions suitable for dressing a specific wound.

Optionally, the method includes providing a support structure upon which said clot forms.

In some exemplary embodiments of the invention, there is provided a kit for preparation of a wound dressing including: (a) a sterile container adapted to receive a volume of blood; (b) sufficient anticoagulant to prevent the volume of blood from clotting; (c) sufficient anti-anticoagulant to cause the volume of blood to clot in the presence of the anticoagulant; and (d) a tray adapted for spreading said volume of blood to a desired thickness.

Optionally, the tray contains a support structure upon which said clot forms.

In some exemplary embodiments of the invention, there is provided a kit or assembly for preparing a dressing to be applied onto a skin injury, comprising one or more hardware components for processing a volume of liquid whole blood to form a sheet of clotted blood.

Optionally, the sheet is of a defined thickness.

Optionally, the kit or assembly comprises one or more of: one or more blood withdrawal devices; one or more blood collection receptacles; one or more receptacles for receiving the blood and forming a clot thereon; one or more support matrices for the formed blood clot; an anticoagulant, optionally already included in the in the blood withdrawal or blood collection devices; and an anticoagulant inhibitor for inducing clot formation.

In some exemplary embodiments of the invention, there is provided a kit for preparation of a wound dressing, the kit comprising: (a) a sterile container adapted to receive a volume of blood; (b) anticoagulant; (c) anti-anticoagulant; (d) a tray for receiving and spreading said volume of blood to a desired thickness and for clotting whole blood therein; and (e) forming a wound dressing comprising the clot.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Percentages (%) of chemicals typically supplied as powders or crystals (e.g. EDTA and calcium salts) are W/V (weight per volume) unless otherwise indicated. Percentages (%) of chemicals typically supplied as liquids (e.g. Citrate solutions and/or diluents) are V/V (volume per volume) unless otherwise indicated.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIG. 1A is a schematic diagram of a patient treated according an exemplary embodiment of the invention:

FIG. 1C is simplified flow diagram illustrating adaptation of exemplary treatment methods to existing treatment modalities;

FIG. 2 is simplified flow diagram illustrating another exemplary treatment method according to some exemplary embodiments of the invention:

FIGS. 6A and 6B are schematic diagrams illustrating an apparatus for clot formation according to some exemplary embodiments of the invention in two different operational states;

FIG. 7 is a schematic diagram illustrating another apparatus for clot formation according to some exemplary embodiments of the invention;

FIG. 8 is a schematic diagram illustrating another apparatus for clot formation according to some exemplary embodiments of the invention;

FIG. 10 is a photograph of an exemplary sheet of clotted whole blood in a receptacle according to an exemplary embodiment of the invention;

FIG. 11 is a photograph of an exemplary sheet of clotted whole blood with embedded support structure supported from the support structure according to an exemplary embodiment of the invention;

FIG. 12 is a photograph of exemplary sheets of clotted whole blood with embedded support structure depicting drainage of liquid from the plates;

FIG. 13 is a photograph of an exemplary sheet of clotted whole blood according to an exemplary embodiment of the invention;

FIG. 14 is a photograph illustrating the sheet of FIG. 13 applied to a skin surface according to an exemplary embodiment of the invention;

DETAILED DESCRIPTION OF EXEMPLARY EMBODIMENTS

Figure 1B:
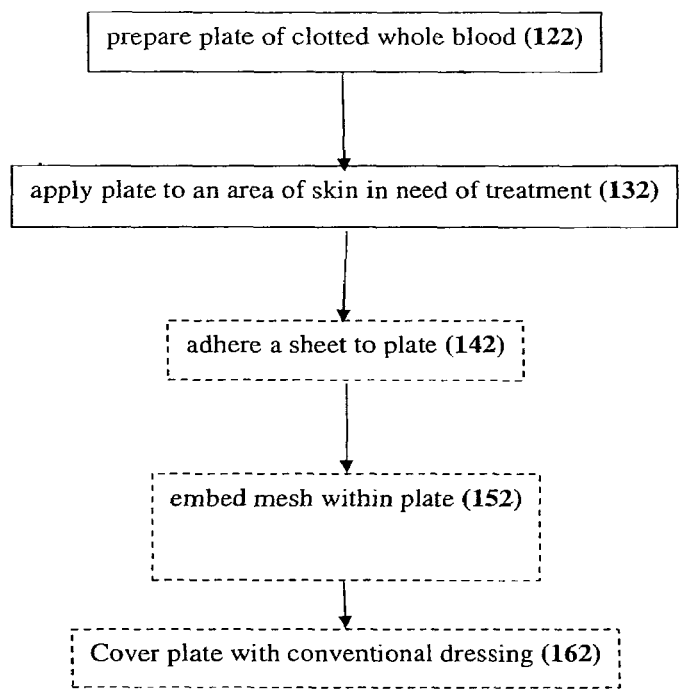
FIG. 1B is simplified flow diagram illustrating an exemplary treatment method according to some exemplary embodiments of the invention.

Embodiments of the invention relate to clotted whole blood containing anticoagulants and anti-anticoagulants, preparation of clotted whole blood and/or use of clotted whole blood in medical treatment and/or preparation of wound dressings and/or storage of clotted whole blood for use as a wound dressing and/or apparatus for preparation of clotted whole blood and/or application of whole blood to skin for in situ clot formation.

Specifically, some embodiments of the invention can be used to burns and/or other skin injuries (e.g. chronic ulcers).

The principles of preparation and use of biological wound dressings and/or apparatus to produce them and/or banks to store them and/or methods of medical treatment relying upon them according to various exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Overview:

FIG. 1A depicts an exemplary embodiment 100 of the invention in which a portion of a skin surface 110 of a subject is covered with plates 120 of clotted whole blood prepared specifically for that purpose. According to various exemplary embodiments of the invention plates 120 may be provided in conjunction with a support structure 130 and/or covered with a conventional dressing 140. The portion of skin surface 110 of the subject covered by plates 120 is selected because it requires treatment (e.g. a burned skin surface).

Plates 120 arranged on skin surface 110 form a biological dressing, whether prepare in advance, or allowed to form in situ at the treatment area. The various embodiments described hereinbelow are united by the idea that non-bleeding wounds (e.g. ulcers and/or burns) are deprived of the natural healing benefits of a scab formed by clotting blood.

Exemplary Treatment Method:

FIG. 1B is a simplified flow diagram of a method of treatment depicted generally as 102. Depicted exemplary method 102 includes preparing 122 one or more plates of clotted whole blood and applying 132 applying the plate(s) to an area of skin of a subject in need thereof (e.g. a burned or ulcerated area).

In some exemplary embodiments of the invention a support layer is adhered 142 to the sheet(s). Optionally, adhering 142 can occur during or after preparation 122. In some exemplary embodiments of the invention, the support layer is constructed to be gas permeable and/or liquid impermeable.

Alternatively or additionally, method 102 includes embedding 152 a mesh within the plate. Typically, embedding is accomplished by contacting liquid whole blood with the mesh and allowing the blood to clot on the mesh. Meshes suitable for this purpose include, but are not limited to fabric meshes (e.g. gauze or cheesecloth or non-woven fabrics). Optionally the mesh contains cotton fibers and/or cellulose.

Alternatively or additionally, method 102 includes covering 162 the sheet with a conventional dressing. The conventional dressing can serve to hold the plate in place and/or preserve sheet integrity and/or absorb exudates emanating from the sheet and/or prevent unwanted contact force (e.g. from donning and/or removing clothing). Optionally, the conventional dressing is changed with a same frequency or greater frequency than the sheet itself.

In some exemplary embodiments of the invention, sterility of the sheet is maintained from formation thereof until application to the skin surface. Sterility can be maintained by any means known in the art.

According to various exemplary embodiments of the invention the sheets are prepared by spreading whole blood in a layer with thickness of 1 mm, optionally 2 mm, optionally 3 mm or intermediate or greater or lesser thicknesses. A sheet of clotted blood will typically be less thick than the original layer of liquid blood.

Exemplary Use Scenarios

FIG. 1C is simplified flow diagram 104 illustrating adaptation of exemplary treatment methods 102 to existing wet treatment 170 and dry treatment 180 modalities.

In some exemplary embodiments of the invention, a wet treatment mode 170 is applied and the sheet is kept moist 124 after preparation 124. The moist sheet is then applied 132 to an area of skin in need of treatment. Optionally, the sheet is covered 134 with a moist dressing and/or covered 136 with a moisture retaining barrier.

In some exemplary embodiments of the invention, a dry treatment mode 180 is applied and the sheet is dried 126 after preparation 124. The dry sheet is then applied 132 to an area of skin in need of treatment. Optionally, the sheet is covered 133 with an absorbent dressing which can optionally be changed 135 so that fluid continues to be drawn from the sheet.

Optionally, a mixture of wet treatment 170 and dry treatment 180 modalities is employed. In some exemplary embodiments of the invention, the sheet is kept moist 124, applied 132 and covered 133 with absorbent dressing. In some exemplary embodiments of the invention, the sheet is dried 126, applied 132 and covered with moist dressing 136.

Additional Exemplary Treatment Method:

FIG. 2 is a simplified flow diagram of another method of treatment depicted generally as 200. Depicted exemplary method 200 includes applying 210 an absorbent covering to an area of skin of a subject in need of treatment (e.g. a burned area). Optionally, the edges of the absorbent covering are masked. Optionally, the absorbent covering includes a mesh such as, for example, gauze or cheesecloth. Opt the mesh contains cotton fibers and/or cellulose.

Depicted method 200 includes applying 220 whole blood to the absorbent covering and allowing 230 the whole blood to clot to form a sheet of clotted whole blood. If optional; masking has been employed, it can serve to direct applied blood preferentially towards the applied absorbent covering.

In some exemplary embodiments of the invention, method 200 includes covering the sheet with a gas permeable material (e.g. nylon and/or cotton and/or polyurethane).

In some exemplary embodiments of the invention, method 200 includes covering the sheet with a conventional dressing as described above for method 102 and/or maintaining sterility of the blood during application 220.

Figure 3:
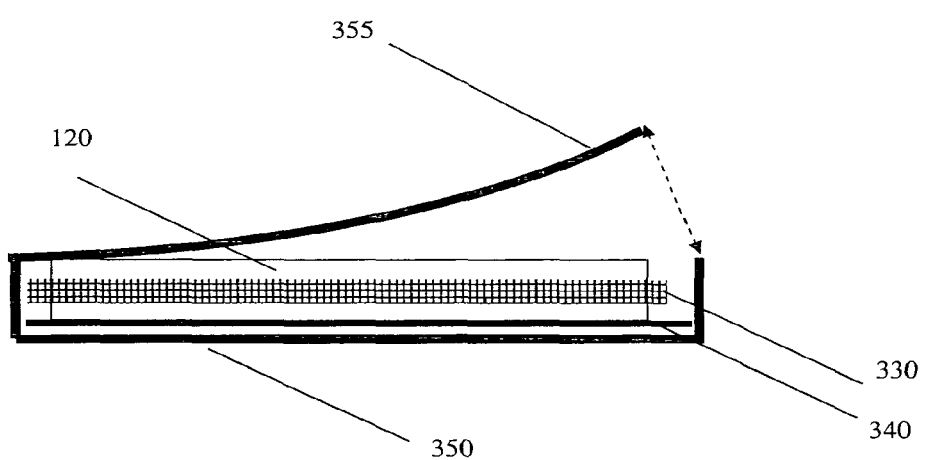
FIG. 3 is a schematic diagram illustrating an article of manufacture according to some exemplary embodiments of the invention.

Exemplary Article of Manufacture:

FIG. 3 is a schematic representation of an article of manufacture depicted generally as 300 viewed in cross section. Depicted exemplary article of manufacture includes a sterile sheet 120 of clotted whole blood. Sheet 120 includes an anticoagulant material dispersed throughout the sheet and a sufficient amount of anticoagulant inhibitor to permit formation of the sheet despite presence of the anticoagulant. Anticoagulants and inhibitors suitable for use in various embodiments of the invention are described hereinbelow.

Sheet 120 is provided in packaging material 350. Depicted exemplary packaging material 350 includes a tearable seal 355 which allows removal of sheet 120 without tools. Packaging material 350 can be provide as an envelope, a shrink wrap, a bubble pack, a sealed tub a jar, a canister or any other packaging form known in the art.

According to various exemplary embodiments of the invention, article of manufacture 300 can be provided at ambient temperature, or provided under refrigeration. Suitable refrigeration temperatures include 12, 8, 4, 0, −20, −70 and −170 degrees centigrade and intermediate temperatures.

According to various exemplary embodiments of the invention, sheet 120 can include an internal support (e.g. mesh 330) and/or an external support 340. Optionally, these support(s) can be used to facilitate removal of sheet 120 from packaging material 350 and/or transfer of sheet 120 to a desired treatment location and/or placement of sheet 120 at the desired location.

Alternatively or additionally, internal support (e.g. mesh 330) and/or external support 340 can contribute to structural properties of sheet 120. Structural properties include tensile strength, compressive strength and elasticity.

Figure 4:
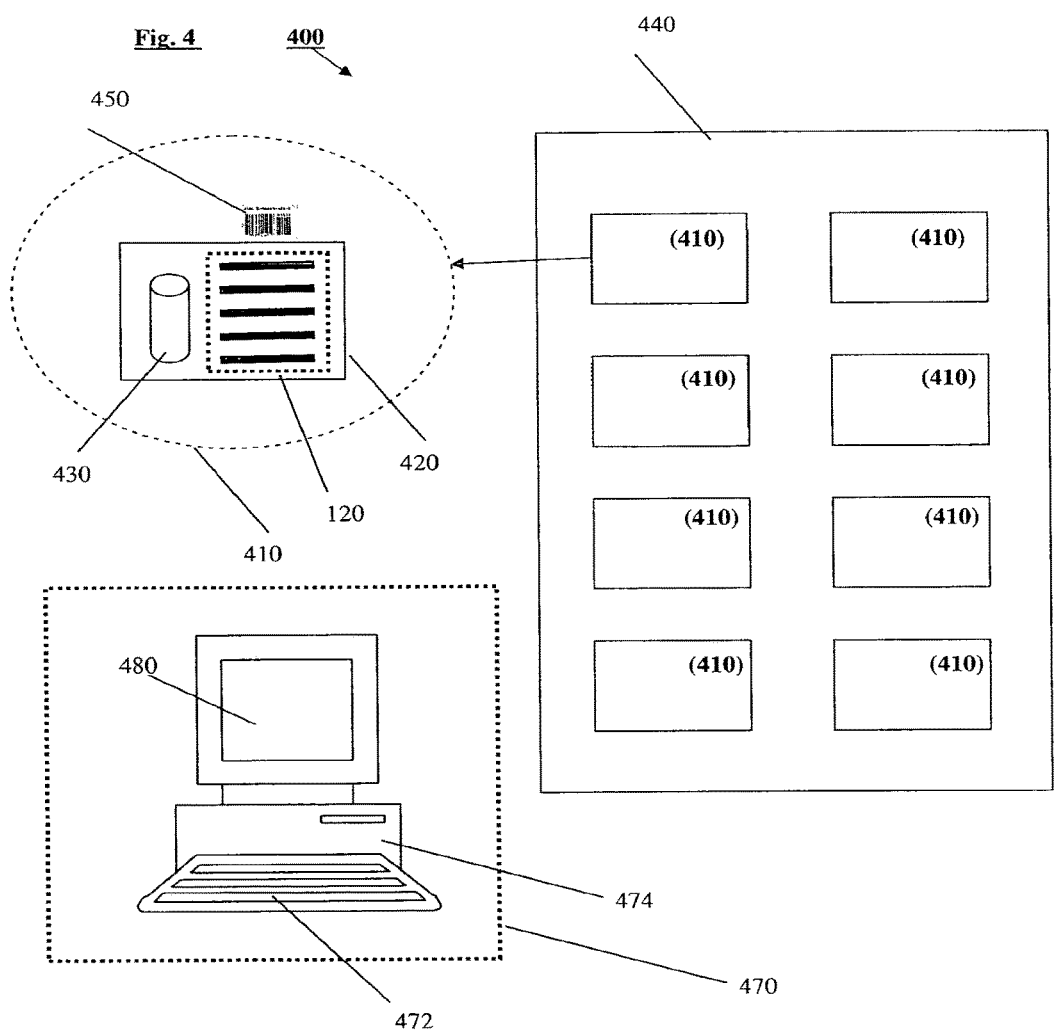
FIG. 4 is a schematic representation of a clot bank according to some exemplary embodiments of the invention.

Exemplary Storage Facility:

FIG. 4 is a schematic representation of a storage facility depicted generally as 400. Depicted exemplary storage facility 400 serves as a bank of biological dressings. Facility 400 includes a plurality of sterile sheets 120 of clotted whole blood, each sheet cataloged by a unique identifier (depicted as a bar code 450) indicating a unit of whole blood from which the sheet was derived. In the depicted exemplary embodiment pates 120 are stored in groups of 5 within storage containers 410. In the depicted embodiment, 5 sheets prepared from a single unit of whole blood are stored together and optionally treated as a single inventory item or 5 separate inventory items. A single storage container 410 is depicted in the inset in detail. In other embodiments of the invention, sheets 120 are stored and catalogued individually.

Storage facility 400 includes a refrigerated compartment 440 containing sheets 120. In the depicted embodiment, 8 containers 410 are depicted in compartment 440 so that a total of 40 sheets are stored. This simplified representation is solely for the sake of clarity of presentation. In actual practice, the number of sheets 120 stored would probably be in the thousands, tens of thousands or even hundreds of thousands.

Optionally, storage temperature and number of sheets stored are interrelated. For example, lower storage temperatures may contribute to longer "shelf life" of sheets 120 which, in turn, contributes to an ability to accumulate a greater number of sheets before they must be discarded.

Optionally, storage of a greater number of sheets contributes to an increased likelihood of finding a suitable match for a subject in need of treatment.

Depicted exemplary storage facility 400 includes cross compatibility information for each of the units of whole blood from which sheets 120 are formed.

In some exemplary embodiments of the invention, the cross compatibility information is provided as machine readable data associated with said unique identifier (e.g. bar code 450) in a look up table in a memory 474 of a computer 470. Optionally, a user enters cross compatibility information from a subject in need of treatment via a suitable user interface (e.g. keyboard 472) and is presented with a list of locations (e.g. on display 480) in refrigerated compartment 440 where suitable sheets 120 can be found. Suitable sheets in this case are "theoretically suitable" based upon a panel of markers. Optionally, a bar code reader (not shown) is used to verify identity of sheets 120 in specific containers 410.

Alternatively or additionally, cross compatibility information is provided as an aliquot 430 of un-clotted blood reserved from each of said units of whole blood from which each of sheets 120 was prepared. Aliquots 430 can be associated with unique identifier 450. In the depicted embodiment, association is physical association resulting from storage in a same container 410 as corresponding sheets 120. According to these embodiments, cross compatibility is checked practically by mixing un-clotted blood from a potential recipient from a sample drawn from aliquot 430 as is known in the art.

Optionally, theoretically suitable sheets are checked practically prior to actual use on a subject.

Optionally, at least some sheets 120 are provided on an external support structure in contact with the sheet and/or at least some of sheets 120 include an internal support stricture (e.g. a mesh embedded in sheet 120).

Figure 5:
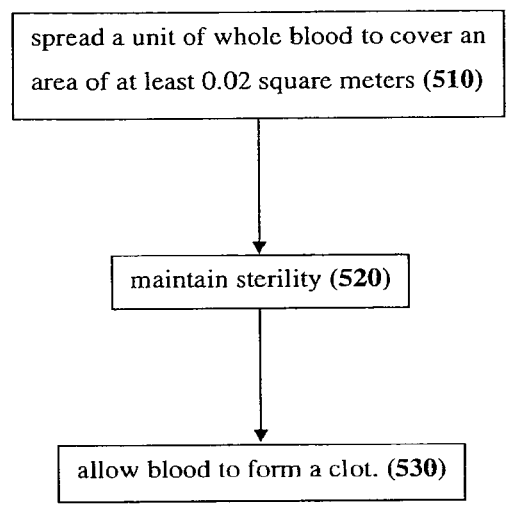
FIG. 5 is a simplified flow diagram illustrating an exemplary manufacturing method according to some exemplary embodiments of the invention.

Exemplary Method of Manufacture:

FIG. 5 is a simplified flow diagram of a method of producing a biological dressing depicted generally as 500. Depicted exemplary method 500 includes spreading 510 a standard unit of whole blood to cover an area of at least 0.02 (e.g. 0.1 or more) square meters while maintaining 520 sterility and allowing 530 the blood to form a clot. According to various exemplary embodiments of the invention, the area may be 0.15, 0.2 square meters or greater or intermediate areas.

In some exemplary embodiments of the invention, method 500 includes adding a coagulation initiator to the whole blood prior to spreading 510. According to various exemplary embodiments of the invention the coagulation initiator is selected to neutralize an activity of an anticoagulant in the unit of whole blood.

Optionally, spreading 510 occurs in a receptacle overlaid with a support layer which prevents) contact between the whole blood and the receptacle as will be described in greater detail hereinbelow. Optionally, the support layer is gas permeable and/or liquid impermeable.

In some exemplary embodiments of the invention, spreading 510 is performed on a mesh which becomes embedded in the clot.

In summary, exemplary embodiments of the invention encompass any use of unfractionated whole blood in manufacture of a wound dressing.

Exemplary Apparatus for Clot Production:

FIGS. 6A and 6B are schematic diagrams illustrating a device for clotting whole blood ex-vivo according to some exemplary embodiments of the invention in two different operational states depicted generally as 600 and 601.

In FIG. 6A, the device is depicted in fully assembled operational state 600 in which it is connected to an external blood source 610 by a connector 612. The depicted exemplary device includes an inlet 614 comprising a channel of fluid communication to an interior of the device and a sample receptacle 650 adapted to spread a sample provided therein to produce a uniform layer 620. Adaptation can include, for example, selection of a suitable material for construction to maintain blood surface tension at a value that encourages spreading. Alternatively or additionally, a surface contacting the blood may be treated with a surfactant and/or textured to encourage spreading. In some exemplary embodiments of the invention, receptacle 650 contains a sufficient amount of an anti-anti-coagulant to cause coagulation of blood introduced into the receptacle.

The depicted exemplary embodiment includes at least one support structure 640 deployed in receptacle 650 so that uniform layer 620 forms on structure 640. Support structure 640 is depicted as an external layer which adheres to a blood clot formed thereupon. Optionally, the layer is permeable to gas and/or impermeable to liquids.

Optionally, a space 642 is provided between receptacle 650 and layer 640 for accumulation of liquids.

Alternatively or additionally, support structure 640 includes a mesh embedded in layer 620 and clot sheet 120 resulting therefrom.

In the depicted embodiment, a removable cover 630 adapted to maintain sterility of layer 620 covers receptacle 650.

In some exemplary embodiments of the invention, the interior of the device is under vacuum pressure. According to various exemplary embodiments of the invention interior volume of the device and/or relative desired fill volume and/or flexibility of materials are considered when calculation an amount of vacuum to apply. Optionally, applied vacuum collapse, or partially collapses the device.

Exemplary Apparatus for Concurrent Production of Multiple Clots:

FIG. 7 is a schematic diagram illustrating a device depicted generally as 700 for clotting whole blood ex-vivo to concurrently form multiple sheets. Depicted exemplary device 700 includes an inlet 710 comprising a channel of fluid communication to an interior of the device and a plurality of sample receptacles 750 (five are depicted, although other numbers of receptacles may be employed) interconnected to allow concurrent inflow from a common source. Each of receptacles 750 is adapted to spread a sample provided therein to produce a uniform layer as described hereinabove.

Depicted exemplary device 700 includes a sterility guard 730 adapted to maintain sterility of the layer in each of stacked receptacles 750. In the depicted embodiment, receptacles 750 are configured as drawers so that removal of one receptacle 750 does not effect sterility of said layer in any other of receptacles 750. Thus, at least some of receptacles 750 serve as sterility guards for another of receptacles 750.

Alternatively or additionally, sterility guard 730 comprises a cover associated with at least some of receptacles 750.

In some exemplary embodiments of the invention, the interior of housing 720 is provided under vacuum.

FIG. 8 is a schematic diagram illustrating a device depicted generally as 800 for clotting whole blood ex-vivo to concurrently form multiple sheets. Depicted exemplary device 800 includes an inlet 810 providing fluid communication to an interior of housing 820.

The interior of housing 820 is divided into a plurality of sample receptacles interconnected to allow concurrent inflow from a common source by spacers 840. In the depicted embodiment interconnection is in parallel, although an alternate arrangement of spacers can be used to provide receptacles in series. Series/parallel combinations are also possible in additional embodiments of the invention.

Each of receptacle is adapted to spread a sample provided therein to produce a uniform layer as described above.

Cover 820 of housing 821 serves as a sterility guard adapted to maintain sterility of the layer in each of the receptacles.

During use, whole blood is loaded via inlet 810 and proceeds through lumen 830 where it is in fluid communication with spaces between spacers 840.

In the depicted exemplary embodiment, spacers 840 serve as external support structure deployed in the receptacles. A layer of liquid whole blood forms on each of support structures 840 which serve as external layers to which a blood clot adheres as it forms thereupon.

In the depicted exemplary embodiment, mesh layers 330 are provided between spaces 840. Mesh layers 330 function as internal support structure embedded in the layer of liquid whole blood, and the blood clot resulting therefrom.

In the depicted exemplary embodiment, device 800 includes an outlet valve 811 providing fluid communication between the interior of housing 820 and an ambient environment. Optionally, valve 811 permits gas to exit the device as it fill with blood. In some exemplary embodiments of the invention, valve 811 is unidirectional and/or filter so that it does not compromise sterility.

In some exemplary embodiments of the invention, the interior of housing 820 is provided under vacuum.

In the devices depicted in FIGS. 7 and 8, each the receptacles can optionally contain a sufficient amount of an anti-anti-coagulant to cause coagulation of blood introduced therein.

Figure 9:
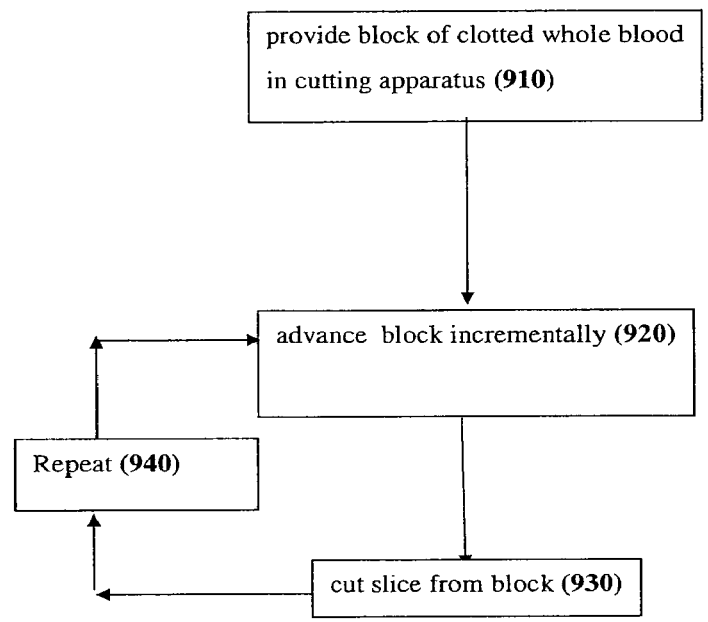
FIG. 9 is simplified flow diagram illustrating an exemplary method of preparing plates of clotted whole blood according to some exemplary embodiments of the invention.

Exemplary Method to Produce Sheets of Clotted Blood from a Block:

FIG. 9 is simplified flow diagram illustrating an exemplary method 900 of preparing sheets of clotted whole blood according to some exemplary embodiments of the invention. Depicted exemplary method 900 includes providing a block of clotted whole blood in a cutting apparatus and advancing 920 the block incrementally. After the incremental advancement, the block is cut 930 to form a slice which becomes a "sheet" as described hereinabove. Advancing 920 and cutting 930 can be incrementally repeated 940 to produce additional sheets.

Sheet thickness can be controlled by adjusting the increment of advancement 920.

Optionally, the block to be cut is frozen to increase hardness.

In some exemplary embodiments of the invention, a relatively small volume of blood (e.g. 10, 20, 30, 40 or 50 ml or intermediate volumes) is collected and clotted in an available container (e.g. test tube or syringe barrel). Optionally, pieces, in the form of slices or sheets are cut from this clot using any available tools (e.g. a scalpel or razor blade. In some exemplary embodiments of the invention, cutting is performed on a marked surface (e.g. graph paper) to keep slices relatively uniform in thickness. This type of method can be employed to treat ulcers with small sizes (e.g. 1, 2, 3, 4 or 5 square centimeter).

Exemplary Materials:

In some exemplary embodiments of the invention, external support layers (e.g. 340 and/or 640) can be constructed of one or more materials including but not limited to nylon, polyurethane, cotton, a silicon and rubber. Optionally, materials are selected to be gas permeable and/or water impermeable.

In some exemplary embodiments of the invention, sheet forming receptacles (e.g. 650 and/or 750) can be constructed of one or more materials including but not limited to glass, polyurethane, polyvinylchloride, polycarbonate, cellulose, polystyrene and a rubber.

In general, materials for construction of clotting devices described hereinabove will be selected to be low cost, light weight and sterilizable. These factors all contribute to feasibility of production of "single use" or "disposable" medical products.

In some exemplary embodiments of the invention, internal supports (e.g. 330) are provided as meshes. Meshes suitable for this purpose include, but are not limited to fabric meshes (e.g. cotton gauze or cheesecloth). In other exemplary embodiments of the invention, non-woven fabrics are substituted for meshes. In other exemplary embodiments of the invention, the internal supports are provided as other types of matrices or scaffolds. Optionally, the mesh includes cotton fibers and/or cellulose.

Exemplary Dimensions:

In some exemplary embodiments of the invention, receptacles are sized to be about 15×20 cm. If a layer of liquid whole blood 3 mm deep is placed in receptacles of this size, a standard unit of whole blood fills 5 receptacles. The aggregate area of the 5 receptacles is 0.15 square meters, which corresponds to 10% of the skin surface of an average individual. A set of five receptacles arranged as deicted in FIG. 7 can be prepared with a total height of about 5 to 8 cm and a footprinf of about 16×21 cm or less.

If larger coverage areas are desired, thinner layers of whole blood and/or a greater number of receptacles can be employed. Optionally, coverage of more than 0.15 square meters involves use of more than 1 unit of whole blood.

In other exemplary embodiments of the invention, such as ulcers, smaller coverage areas are sufficient. Optionally, collection of small volumes of blood (e.g. 3, 5, 10, 20 or 30 cc or smaller or intermediate volumes) is sufficient to prepare a clot to cover an ulcer. In some exemplary embodiments of the invention, correspondingly smaller clotting trays and/or thinner clots are employed.

Exemplary Anticoagulants and Anticoagulant Inhibitors:

Anticoagulants suitable for use in the context of the present invention include, but are not limited to EDTA (ethylenediaminetetraacetic Acid), EGTA (ethylene glycol tetraacetic acid), Citrate (sodium citrate or acid citrate dextrose), Heparin and oxalate.

Anticoagulants inhibitors suitable for use in the context of the present invention include, but are not limited to $Ca^{2+}$, $Mg^{2+}$, Kaolin, negatively charged phospholipid (PL) and protamine sulfate. Table 1 summarizes exemplary ways in which clotting time can be controlled to obtain a desired working window (e.g. for preparation of sheets 120).

TABLE 1

Exemplary in vitro clotting times

| Tested material | Clotting time |
| --- | --- |
| Whole blood | 4-8 min |
| Whole blood + EDTA or citrate | Infinite |
| Citrated whole blood + $Ca_{++}$ | 2-4 min |
| Citrated whole blood + PL (negatively charged phospholipids) + $Ca_{++}$ | 60-85 sec |
| Citrated whole blood + kaolin + PL + $Ca_{++}$ | 21-32 sec (aPTT) |
| Citrated whole blood + thromboplastin + $Ca_{++}$ | 11-12 sec (PT) |

In some exemplary embodiments of the invention, whole blood with an anticoagulant added is obtained from a blood bank and sufficient anticoagulant inhibitor is added to achieve a clotting time of 2 to 8, optionally 4 to 8, minutes. This time is deemed sufficient to allow distribution of the unit of blood in receptacles as a liquid for subsequent clotting therein as described above.

Additional Exemplary Method

In some exemplary embodiments of the invention, a method of preparing a wound dressing includes collecting a volume of blood and clotting the blood ex vivo to form a clot. Optionally, the collected volume is small (e.g. 5, 10, 15 or 20 ml or intermediate or lesser volumes). In some exemplary embodiments of the invention, the volume to be collected is determined in consideration of an area of a wound to be treated. Optionally, the method includes cutting a portion of the clot to dimensions and/or shape suitable for dressing a specific wound. Cutting may be for example with scissors. Optionally, the method includes providing a support structure upon which said clot forms. Support structures can be internal and/or external as described hereinabove.

Exemplary Kits:

Some exemplary embodiments of the invention relate to kits for preparation of a wound dressing including clotted whole blood. Optionally, the kit includes a sterile, or sterilizable, container adapted to receive a volume of blood and sufficient anticoagulant to prevent the volume of blood from clotting. The container can be, for example, a syringe, a bag or test tube (e.g. a vacuum filled test tube).

In some exemplary embodiments of the invention, the anticoagulant is provided in the container. Optionally, the kit includes sufficient anti-anticoagulant to cause the volume of blood to clot in the presence of the anticoagulant. Addition of the anti-anticoagulant to the blood with anticoagulant begins a window of time during which clotting occurs. During this window of time, the blood is transferred to a tray adapted for spreading the volume of blood to a desired thickness. Suitable thicknesses include 1, 2, 3, 4 and to 5 mm and intermediate or greater thicknesses.

Optionally, the tray contains a support structure upon which said clot forms. Support structures can be internal and/or external as described hereinabove.

Kits of this type can be used by individuals and/or by medical practitioners. Optionally, a user prepares several dressings at a time and stores some or all of them for future use.

Exemplary Advantages:

According to various exemplary embodiments of the invention use of clotted whole blood sheets 120 as described hereinabove promotes wound healing and/or reduces incidence of infection and/or contributes to a reduction in debridement frequency and/or reduces scarring. These advantages are believed to be most significantly realized in non-bleeding wounds such as burns and chronic ulcers (e.g. diabetic foot ulcers). These advantages are believed to be available, at least to some degree, without regard to the source of blood for sheets 120.

Exemplary Blood Sources

According to various exemplary embodiments of the invention blood used to form sheets 120 can be autologous blood, homologous whole blood received from a blood bank or pooled homologous whole blood or pooled heterologous whole blood. It is generally accepted in medical practice that a healthy individual can donate 1 unit of whole blood about every 6 to 8 weeks without adverse effects. Alternatively, a single individual can donate smaller amounts of blood at higher frequency.

In some exemplary embodiments of the invention, a subject in need of treatment (e.g. a burn victim with burns over 8% of their body surface) donates a unit of whole blood which is subsequently used to form sheets 120 using methods and/or devices as described hereinabove. This treatment strategy can contribute to a reduction in risks associated with incompatibility between blood donor and treated subject. However, there is a practical limitation as to how much skin surface can be treated with an autologous donation and/or whether a subsequent autologous donation will be available for continuation of therapy. These factors will each, in turn, be influenced by thickness of sheets 120 as described in greater detail hereinbelow.

In some exemplary embodiments of the invention, a subject in need of treatment (e.g. a burn victim with burns over 16% of their body surface) is treated with sheets 120 prepared from homologous (e.g. human) blood using methods and/or devices as described hereinabove. This treatment strategy may slightly increase risks associated with incompatibility between blood donor and treated subject. However, it is less limited with respect to how much skin surface can be treated and/or availability of additional sheets for continuation of therapy.

In other exemplary embodiments of the invention, homologous (e.g. human) blood from many units is pooled to form a large volume which is subsequently used to form sheets 120 to treat subjects in need thereof as described hereinabove. This treatment strategy is very amenable to industrial scaling and reduces time and labor associated with cross compatibility screening. However, a degree of risk associated with incompatibility between blood donor(s) and treated subject remains to be assessed. This treatment strategy is virtually unlimited with respect to how much skin surface can be treated and/or availability of additional sheets for continuation of therapy. There is a possibility that pooling of a large number of different types of blood prior to clotting to form sheets 120 may result in a "universal donor" situation as antibodies and antigens bind and neutralize one another prior to clot formation.

In other exemplary embodiments of the invention, heterologous (e.g. porcine or equine) blood from many units is pooled to form a large volume which is subsequently used to form sheets 120 to treat subjects in need thereof as described hereinabove. Alternatively or additionally, a pool of human blood may be extended by mixing with heterologous blood. This treatment strategy is also very amenable to industrial scaling and reduces time and labor associated with cross compatibility screening. However, a degree of risk associated with incompatibility between clots derived from one or more heterologous species and treated subjects remains to be assessed. This treatment strategy is also virtually unlimited with respect to how much skin surface can be treated and/or availability of additional sheets for continuation of therapy. As with pooled homologous blood, there is a possibility that pooling of blood from multiple unrelated species (e.g. porcine, ovine and equine and canine blood) prior to clotting to form sheets 120 may result in a "universal donor" situation as antibodies and antigens bind and neutralize one another prior to clot formation.

Explanation of Sheet Thickness as a Treatment Limitation

In some exemplary embodiments of the invention, a unit of whole blood is spread over an area of 0.1 square meters or more and allowed to clot is described hereinabove. The area which can be covered depends on desired clot thickness after clotting. Table 2 summarizes exemplary coverage areas (% total body area) from a single standard unit of whole blood in terms of initial layer thickness and resultant clot thickness.

TABLE 2

% body surface coverage as a function of liquid whole blood layer thickness

| example | Liquid blood thickness (mm) | Clot thickness (mm) | Total area ($M^2$) | Body surface % |
|---|---|---|---|---|
| 1 | 3 | 1.2 | 0.15 | 10 |
| 2 | 9 | 0.8 | 0.23 | 15 |
| 3 | 1.5 | 0.6 | 0.30 | 20 |
| 4 | 1 | 0.4 | 0.45 | 30 |
| 5 | 0.5 | 0.2 | 0.90 | 60 |

The summary in table 2 makes it clear that there is a linear relationship between how much body surface can be covered by a unit of whole blood and the initial thickness of the whole blood layer used to prepare sheets 12. In some exemplary embodiments of the invention, internal support layers (e.g. mesh 330) and/or external support layers (e.g. 130 and/or 640) and/or conventional dressing (e.g. 140) contribute to a reduction in liquid blood thickness and/or clot thickness which are compatible with therapy efficacy.

In the context of burn treatment, achievement of larger coverage areas can be critical. In the context of ulcer treatment, large coverage area is less important, although the relationship between coverage area and thickness remains.

General

It is expected that during the life of this patent many new anticoagulants and their corresponding inhibitors as well as polymeric plastics will be developed and the scope of the invention is intended to include all such new technologies a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize a wound dressing, an apparatus or kit or article of manufacture and features used to describe a wound dressing, an apparatus or kit or article of manufacture can be used to characterize a method.

It should be further understood that the individual features described hereinabove can be combined in all possible combinations and sub-combinations to produce additional embodiments of the invention. The examples given above are provided solely for purposes of illustration and are not intended to limit the scope of the invention which is defined solely by the following claims. Specifically, the invention has been described in the context of chronic ulcers and/or burn treatment but might also be used to treat other types of skin wounds.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of the present invention will become apparent to one ordinarily skilled in the art upon examination of the following examples, which are not intended to be limiting. Additionally, various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Materials and Methods

The following materials and methods are used in performance of experiments described in examples hereinbelow:

Clotting trays were constructed of from disposable plastic food service sheets with dimensions of size 1 cm×12 cm×8 cm for purposes of experimentation. In actual practice, other sizes and/or materials may be employed. In some exemplary embodiments of the invention, Biocompatible and/or sterilizable plastic polymers are employed.

Saran rap (polyvinylidene chloride [PVDC] made by S. C. Johnson & Son.; USA) was used to cover clotting trays to reduce a tendency of clots to stick to the trays.

Surgical gauze (24×20 mesh, manufactured for M. Feingresh & Co. Ltd) was employed as an exemplary embedded support structure. A double layer of cotton gauze was cut to 9 cm×13 cm or larger for the described clotting trays.

Calcium Gluconate (B. Braun Melsungen AG; Germany) refers to 10 ml ampoules of 10% containing Calcium Gluconate H2O 940 mg; Calcium D-Saccharate 4 H2O 50 mg and water for injection. Each 1 ml provides 0.23 mol Ca++.

Kaolin (Imerys Minerals; Australia PTY) was used as a powder.

Blood was collected from a human volunteer using commercially available blood donation bags with citrate anticoagulant included. For non-citrated controls, blood was collected in a disposable syringe. Indicated volumes were placed in cups and mixed with anticoagulant inhibitors as indicated hereinbelow by swirling then immediately poured into clotting trays.

Blood donation bags were Sterile Non pyrogenic Single use infusion sets (MacoPharma; France) containing 63 ml CPDA1 (Formula for 1 L: Acid citric Monohydr. 3.27 gr, Natr. citras dihydr. 26.3 g; Mononatr. Phosphas dihydr. 2.51 g; Dextr. Monohydr. 31.9 g; Adenin HCL 0.349 g and Water to 1000 ml [Ph 5.6+–0.3; 285 mmol Na/L]).

Example 1

Impact of Coagulants and Anticoagulants on Clot Formation

In order to assay the effects of citrate based anticoagulants and antagonists thereof on clot formation, various combinations were tested. Un-citrated whole blood (tray 2) served as a negative control. Citrated whole blood with no antagonist (tray 1) served as a positive control. Experimental combinations of trays 3, 4, 5 and 6 are detailed in table 3. Antagonist ingredients were mixed briefly in a plastic cup by swirling and poured over pre-cut surgical gauze placed in clotting trays lined with saran wrap to a depth of 4 mm. FIG. 10 is a photograph 1000 of an exemplary clot in a clotting tray with embedded support structure protruding from the edges 7 minutes after addition of calcium gluconate. At this time point, there was no visually perceptible difference between trays 3, 4, 5 and 6.

TABLE 3

Experimental coagulant/anticoagulant combinations

| Tray | Blood volume (ml) | citrated | Calcium Gluconate (ml) | Kaolin |
|---|---|---|---|---|
| 1 | 44 | YES | None | None |
| 2 | 44 | NO | None | None |
| 3 | 40 | YES | 4 | None |
| 4 | 40 | YES | 8 | None |
| 5 | 40 | YES | 4 | 20 mg |
| 6 | 40 | YES | 8 | 40 mg |

Following clot formation, each clot was transferred by means of its embedded support structure to a larger angled tray. FIG. 11 is a photograph 1100 of one of the clots being transferred. Clots were observed for color and texture. Exuded fluid was characterized with respect to volume and appearance. Negative control Tray 1 remained un-clotted and was not involved in further manipulation and/or observation.

FIG. 12 is a photograph 1200 of representative clots in angle trays. Fluid exudate is clearly visible in several trays.

After 12 Minutes from the time the calcium gluconate (and Kaolin where applicable) were added to the citrated blood:

Tray 2 contained a clot that was dark red, soft and thinner than the original 4 mm liquid depth. About 10 ml-13 ml of red fluid exudates collected in the angled tray and clotted.

Tray 3 contained a clot which was less dark red and more solid and thicker than the original 4 mm liquid depth. About 0.5 ml of red fluid exuded and did not clot.

Tray 4 was similar to tray 3.

Tray 5 was similar to trays 3 and 4, but the clot was more solid and thicker than trays 3 and 4. There was less volume of red fluid than trays 3 and 4.

Tray 6 contained a clot that was darker, more rigid and thicker than observed in other trays. There was less red fluid exuded than all other trays, and the color of the fluid was lighter than observed in other trays.

After 23 Minutes from the time the calcium gluconate (and Kaolin where applicable) were added to the citrated blood, each clot was transferred by means of its embedded support structure to a clean larger angled tray. All clots where easily removable from their trays and kept their shape during transfer.

Tray 2 contained a dark red clot which was not rigid and was about 2 mm or less in thickness. This clot continued to exude red fluid at a rate of about 1 m/5 minutes. This clot exhibited axial translation with respect to the embedded support structure indicating an insufficient degree of adhesion.

Trays 3, 4, 5 and 6 the clots were a lighter red than tray 2 and were very solid and thicker than the original 4 mm liquid depth. Small amounts of pale red fluid continued to exude.

Tray 6 contained a clot with the best performance in terms of shape retention, thickness preservation, rigidity and fluid retention.

After 37 minutes each clot was transferred by means of its embedded support structure to a scale for weighing. The citrated clots of trays 3, 4, 5 and 6 weighed about 30% moiré than the positive control clot of tray 2.

Based upon these observations, 8 cc calcium gluconate does not seem to improve clot properties relative to over 4 cc calcium gluconate Kaolin, at either amount, seems to improve clot properties.

In this experiment, properties of the fresh whole blood clot (Tray 2) where judged inferior to citrated coagulated whole blood clots.

About 42 Minutes after addition of anticoagulant antagonists:

FIG. 13 is a photograph 1300 of the clot of Tray 6. This clot was placed in a standard freezer (−20 degrees C.) for 5 days, taken out and placed on the skin of the thigh and fixed in place with medical adhesive, and covered with layers of cotton.

FIG. 14 is a photograph 1400 of the clot of Tray 3 which was subsequently placed on the skin of the thigh and fixed in place by layers of gauze held by adhesive tape and covered with layers of cotton held with additional adhesive tape.

All other clots where left to dry in open air

Preliminary testing of clotted whole blood as a wound dressing material is described below in Examples 2 and 3.

Results presented in this example indicate that embedded support structure were useful in preserving clot integrity and/or shape and/or in facilitating transfer and/or handling.

This example illustrates that it is feasible to prepare sheets of clotted whole blood in desired sizes and shapes for use in various exemplary embodiments of the invention as described hereinabove.

Example 2

Exemplary Use of a Sheet of Freshly Clotted Blood in Preparation of a Wound Dressing In order to evaluate the possibility of using sheets of clotted whole blood as part of a wound dressing, the clot from tray 3 was placed on the skin (FIG. 14) of the thigh and covered with layers of surgical gauze and then layers of cotton held in place with adhesive tape.

Figure 15:
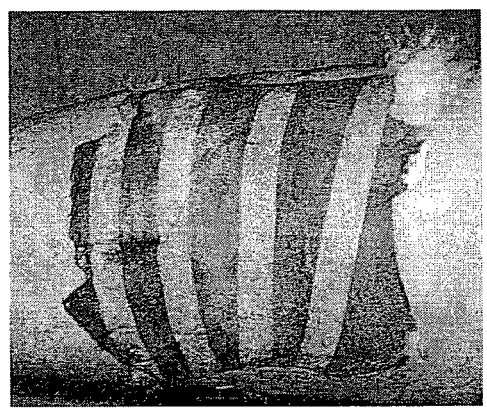
FIG. 15 is a photograph illustrating exudation of liquids from the sheet of FIG. 13 after application to the skin surface in FIG. 14.

After 12 hours, the cotton was removed. FIG. 15 is a photograph 1500 showing that exudates from the clot has soaked through the surgical gauze laid over the clot. It appears that clot exudates soaked into the overlaid gauze made this material part of the clot layer.

This example illustrates that clotted whole blood adheres well to intact skin. The intact skin is used as a model for non-bleeding wounds (e.g. burns and/or ulcers) so the results confirm feasibility of using clotted whole blood as a dressing for non-bleeding wounds. Optionally, dressings according to exemplary embodiments of the invention can be applied to bleeding wounds as well.

Example 3

Effect of Blood Clot Applied to Intact Skin Surface

Figure 16A:
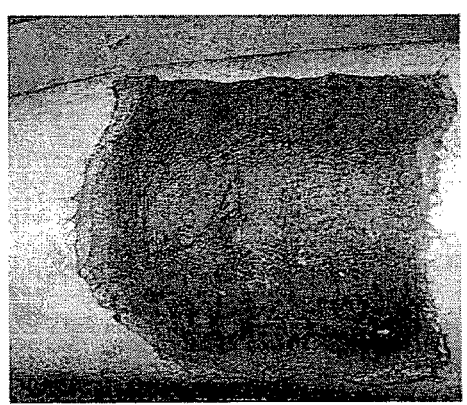
FIGS. 16A, 16B and 16C are a series of photographs illustrating adherence of the fully dried sheet to skin (FIG. 16A) and its removal by peeling (FIGS. 16B and 16C) according to an exemplary embodiment of the invention.
Figure 16B:
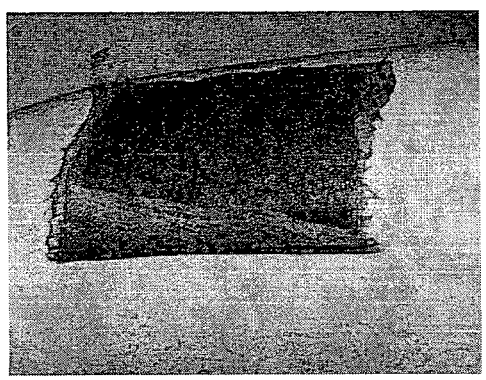
Figure 16C:
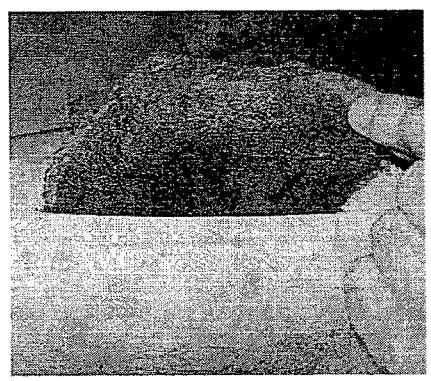

Following example 2, the clot was manually removed from the intact skin surface to which it had been applied. FIG. 16A is a photograph 1600 showing the dried clot adhered to the skin. FIG. 16B is a photograph 1602 peeling of the dried clot from the skin. FIG. 16C is a photograph 1604 showing that removal of the dried clot from to the skin caused no perceptible irritation. Removal was manual by peeling and gentle pulling as seen in FIG. 16C.

The clot was thin and completely dry at this stage. Small defects in the form of holes were observed in the clot. The holes appeared to correspond to places where the internal support structure (gauze) had been broken or torn.

This example illustrates that use of sheets of clotted whole blood in the context of burn treatment provides an alternative to conventional methods. Optionally, sheets of clotted whole blood contribute to a reduction in wound debridement.

Example 4

Exemplary Use of a Sheet of Frozen Clotted Blood in Preparation of a Wound Dressing In order to demonstrate that clots can be prepared in advance and stored for later use as wound dressings, the clot from tray 6 (FIG. 13) was stored frozen for 5 days then thawed at room temperature. The clot was used to prepare a wound dressing as in Example 3. Results were substantially the same as in example 3.

This example illustrates that storage of blood clots prior to their use as wound dressings according to exemplary embodiments of the invention is feasible.

Example 5

Additional Observations on Air Dried Blood Clots

In order to evaluate the potential of storing clotted whole blood under ambient conditions, clots from trays 2, 4 and 5 were left to dry in open air for 25 hours. Compared to the bandaged clots, the air dried clots were thicker, although they became completely dry. These clots were characterized by a very dark red color and were without defects (holes). These clots were odor free.

Example 5 illustrates that it is feasible to store clotted whole blood at ambient temperatures for at least 1 day. The absence of odor suggests no putrefaction. It is not clear whether the absence of holes results from a decrease in handling or other factors.

In general the air dried clots were thicker and maintained more blood elements than those applied as bandages (examples 3 and 4).

Example 6

Treatment of Actual Wounds in Human Subjects

In order to confirm that clotted whole blood can be efficaciously employed as a wound dressing, human subjects with actual wounds of various types were recruited and treated using dressings prepared substantially as described above.

Consecutive patients referred to the Palliative care department and to the nursing departments of the Shoham Geriatric Medical Center (Pardes-Hanna; Israel) were screened for recruitment between June 2009 and December 2009. All potential subjects were already under treatment for their wounds with previously accepted standard of care treatment. The study was approved by Institution review board. In total 7 wounds with etiology stages 2-3 from 6 patients (2 males and 4 females) were dressed clotted whole blood dressings according to exemplary embodiments of the invention. Subjects or their legal guardians signed informed consent forms prior to inclusion in the study. Recruitment criteria were age 18-100, wounds stages 2-3 and informed consent. Exclusion criteria were wounds larger than 8 cm by 8 cm, Cancerous wounds, inability to provide 30 cc blood per week and a proven sepsis established by a blood culture in the past 2 weeks. All ongoing wound localized care treatments were stopped prior to initiating treatment according to an exemplary embodiment of the invention. Wound characteristics are summarized in table 4. The Typing and staging was according to previously published criteria (NPUAP pressure ulcer staging 2007. [npuap.org]. Prevention and treatment of skin tears K. Leblanc et al, Wound Care Canada, Volume 6, Number 1, 2008).

TABLE 4

| Wound characteristics | | | | | |
|---|---|---|---|---|---|
| Wound | Age/Gender | Type/etiology | Location | Size cm$^2$ | Stage |
| 1 | 93/F | Tear wound | Left lower leg | 28.1 | 3 |
| 2 | 88/F | Venous ulcer and fistula | Right foot back | 3.12 | NA |
| 3 | 88/F | Venous ulcer | Left upper foot | 1.6 | NA |
| 4 | 48/F | Pressure ulcer | Right heel | 3.61 | 3 |
| 5 | 32/M | Amputated finger tip | Middle finger | 0.89 | 3 |
| 6 | 90/M | Pressure ulcer | Left heel | 4.7 | 3 |
| 7 | 65/F | Traumatic wound | Right Shin | 2.8 | 2 |

Dressings based upon clotted whole blood were prepared using a kit according to an exemplary embodiment of the invention. The exemplary kit contains 3 sizes of sterile single use clotting trays, small (14.5 cm$^2$), medium (26.4 cm$^2$) and large (64 cm$^2$). Each clotting tray is fitted with medical cotton gauze stretched across the bottom of the tray. As explained hereinabove the gauze becomes embedded in the clot as it forms. Optionally, the gauze contributes to robustness of the dressing and/or simplifies transfer of the dressing to the wound and/or makes trimming to shape easier.

For each wound treatment, wound size was determined by measuring the maximum length between two points on the wound edges. According to the determined size, an appropriate tray was selected (e.g. by the nurse). The clotting tray was selected to be larger than the wound in order to ensure that the clotted whole blood dressing would cover the whole wound area and beyond, at least 0.5 cm of the intact skin around the wound. Specific instructions for the amount of, CPDA1, whole blood and the coagulation activating calcium and kaolin mixture were provided as part of the kit for each of the three sizes of clotting trays: small, medium and large. The exemplary amounts are CPDA1 (1.5 ml, 2 ml and 4 ml), amount of whole blood to be extracted (10 ml, 13 ml and 30 ml) and amount of coagulation activator, the calcium and kaolin mixture (2 ml, 2.5 ml and 5 ml).

Optionally, preparation of the wound bed for dressing was conducted according to accepted procedures, e.g. washing with sterile saline and/or debridement depending on wound type and/or stage. The patient and wound current and past clinical status were documented and the wound was photographed while holding a single use ruler next to the wound edges as a means of monitoring treatment progress.

A syringe (20 ml or 50 ml syringe according to the selected tray) was filled with the appropriate amount of CPDA1 and used to extract venous blood from the patient. Blood withdrawal and handling was performed according to the Hospital precautions guidelines.

In parallel, 5 ml calcium gluconate (B. Braun, Germany) was mixed in a sterile vial with 35 mg of sterile kaolin white powder (Merck). The desired amount (as described above) of coagulation activating mixture was extracted from the vial using the syringe containing blood/anticoagulant mixture. The contents of the syringe were gently mixed for 10 seconds to induce coagulation.

At this point, the coagulating blood was transferred into the pre selected clotting tray and the tray was placed on a flat horizontal surface. The nurse then waited (e.g. about 10 minutes) for the dressing including a sheet of clotted whole blood to form. At this stage, the clotting tray is opened using sterile gloves and clotted whole blood based dressing is transferred to the wound, placing it on the wound so the embedded pad faced upwards. The dressing according to an exemplary embodiment of the invention was then affixed to the wound by covering it with a non adhesive pad, then gauze and then it was wrapped by an elastic bandage or by using a Band Aid™ (Johnson & Johnson, Somerville, N.J.).

Following initial treatment, a follow up program including two types of visits was implemented. In a first "monitoring" type of visit, the exemplary whole blood clot based dressing was not removed from the wound. In a second "re-application" visit the exemplary whole blood clot based dressing was removed and a new whole blood clot based dressing was created and applied as described above.

Monitoring visits were conducted every 2 days. In these sessions the dressing according to an exemplary embodiment of the invention was not removed, but only the gauze pads above the clot. The visit included visual inspection of the exposed surface of the dressing according to an exemplary embodiment of the invention to document the adherence of the clot to the wound, visual inspection of the wound periphery for adverse events and olfactory inspection to monitor for possible infection.

Regular re-application visits were scheduled every 6 to 8 days depending on the staff availability. The dressing changes were pre-scheduled in order to document the wound healing process underneath. In the two trauma wounds treated, the clotted whole blood dressing was left on the wound until it naturally dropped off. These wounds were not chronic ulcers. Re-application visits included documentation, photographing (of the existing dressing and the wound being treated) and removal and replacement of the clotted whole blood based dressing according to an exemplary embodiment of the invention. The Re-application visit also included wound bed preparation according to standard procedures using gauze and saline.

In this study, treatment continued until complete healing of the wound or until clinical determination that the wound could not further improve without additional invasive procedures, such as surgery of a fistula, procedures which are not performed in the geriatric center.

All kit components and materials were supplied as sterile single use items with regulated and pre-measured materials. The whole kit is disposable and was discharged according to the hospital regulations. Throughout the study measures were taken to prevent the clot from getting wet (e.g. using plastic wrap such as CLING-FILM™ or SARAN WRAP™ to wrap the limbs and specially dedicated waterproof adhesive pads to protect the wound during bathing).

Wounds were photographed during the healing process using a digital camera (Cannon Power Shot A590) using a flash, at a defined distance of 50 cm from the wound, facing the front of the wound. In each photograph a disposable reference ruler was placed in close proximity to the wound edges. The ruler included the date, patient number and wound study number as filled in by the research staff.

The wound pictures where analyzed by using NIH Image analysis software "ImageJ" (National Institute of Health, Bethesda, Md., USA) which is available for download at http://rsb.info.nih.gov/ij/download.html. This software is in the public domain. According to other exemplary embodiments of the invention, commercial image analysis software products are employed instead of Image J.

Image analysis in this case included:
a. measurement of the number of pixels in 10 mm as presented in the picture reference ruler.
b. delineations of the wound edges and documentation of automatic pixels area output of the image.
c. repeating step b three times.
d. calculating the average pixels area of the 3 separate delineations,
e. transformation of the pixels area to $mm^2$ area by the measured pixels per 10 mm.
f. documentation of the final result in the patients CRF for the specific date the picture was taken.

Optionally, other image analysis strategies can be substituted for this strategy.

The clinical results of dressing wounds with clotted whole blood dressings according to exemplary embodiments of the invention are presented in table 5. Five out of seven wounds were totally healed and the remaining two were mare than 80% healed. Five out of seven wounds were moderately to heavily exudating at the onset of treatment with dressings according to exemplary embodiments of the invention. In all of the exudating wounds, the extraction of the exudates through the clotted whole blood based dressing and its absorbance in to the covering pads was documented. This demonstrates that dressings according to exemplary embodiments of the invention are not occlusive. On average there was a dressing application every 8.8 days. The cases are presented below.

Figure 18A:
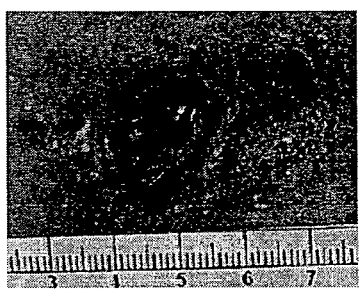
Figure 18B:
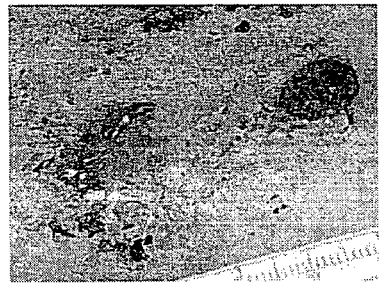

FIG. 18 illustrates a case of a vascular wound diagnosed with an exudating fistula 1 cm next to the main wound which required surgical procedure before treatment (FIG. 18A) and after treatment (FIG. 18B). The photographs indicate that the main wound showed complete and good healing, while the exudating fistula did not completely heal although it was covered with the same dressing according to an exemplary embodiment of the invention for the same period of time. Therefore the total wound including the fistula was calculated as only 80% healed.

Figure 19A:
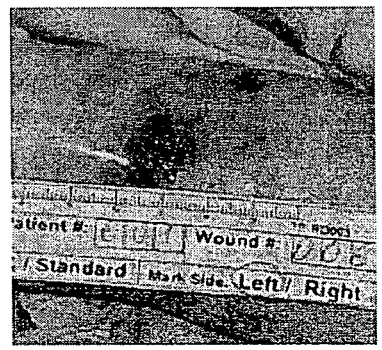
Figure 19B:

FIG. 19 illustrates a case of a venous ulcer on the left upper foot prior to treatment (FIG. 19A) which was completely healed (FIG. 19B) by 11 days of treatment with a dressing according to an exemplary embodiment of the invention.

Figure 20A:
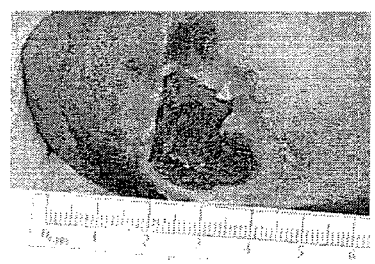
Figure 20B:
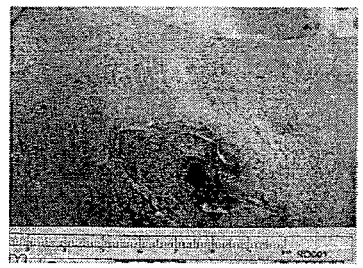

FIG. 20A depicts a pressure ulcer in which treatment was stopped after 82% closure (FIG. 20B), due to re-opening of the wound that resulted from recurrent direct pressure on the wound when it was not dressed with the dressing according to an exemplary embodiment of the invention.

Figure 17A:
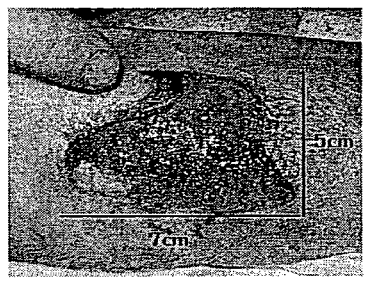
FIGS. 17A, 17B, 18A, 18B, 19A, 19B, 20A, 20B, 21A, 21B, 22A, 22B, 23A and 23B are a series of photographs illustrating wounds prior to treatment (panel A in each figure) and after treatment with a wound dressing according to an exemplary embodiment of the invention (panel B in each figure).
Figure 17B:
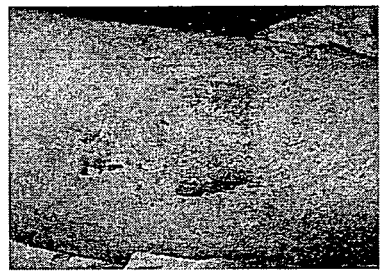
Figure 21A:
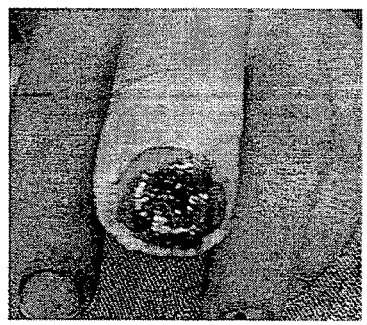
Figure 21B:
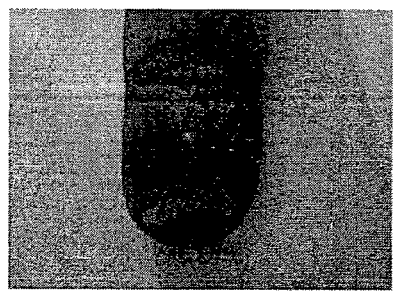

The two trauma wounds, a case of left shin laceration (tear wound) in a 93 year old woman (FIG. 17A pre-treatment) and a right hand middle finger tip amputation in a 34 years old male (FIG. 21A pre-treatment) had a single application of the dressing according to an exemplary embodiment of the invention, which lasted for 21 days (laceration) and 19 days (amputation), until the dressing dropped off, healing was achieved without the need of further dressing (see FIGS. 17B and 21B respectively).

Figure 22A:
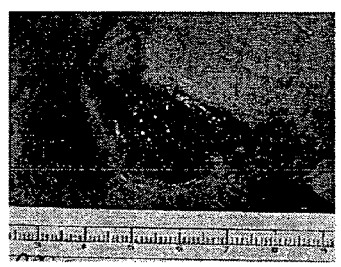
Figure 22B:
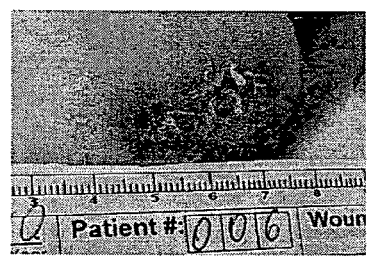
Figure 23A:
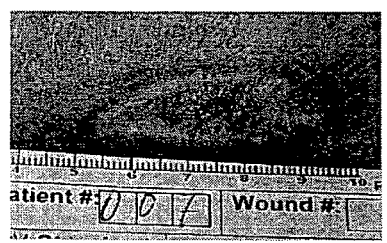
Figure 23B:
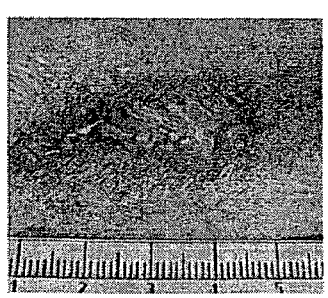

There were two cases of ulcers in patients with diabetes, one pressure ulcer on the left heel (FIG. 22A pre-treatment) and the other a traumatic wound on the right shin (FIG. 23A), the healing of ulcers in diabetic patients was similar to the healing on non diabetic patients (See FIGS. 22B and 23B respectively).

TABLE 5

Treatment Results

| Wound | Size (cm$^2$) pre-treatment | Size (cm$^2$) post-treatment | Days (applications)* | FIG. |
|---|---|---|---|---|
| 1 | 28.1 | 0 | 21 (1) | 17 |
| 2 | 3.12 | 0.71 | 61 (7) | 18 |
| 3 | 1.09 | 0 | 11 (1) | 19 |
| 4 | 3.61 | 0.64 | 36 (5) | 20 |
| 5 | 0.89 | 0 | 19 (1) | 21 |
| 6 | 4.7 | 0 | 49 (7) | 22 |
| 7 | 2.8 | 0 | 7 (1) | 23 |

*days dressed with clotted whole blood dressing (number of dressing applications)

Results presented in this example clearly demonstrate that a care provider can effectively and safely prepare a clotted whole blood dressing according to exemplary embodiments of the invention, optionally from a kit provided at the point-of-care and containing pre-measured components and/or tools associated with preparation of the dressing.

Alternatively or additionally, results presented in this example clearly demonstrate that dressing wounds with a dressing including an autologous blood clot is safe for use in chronic wounds of various etiologies. No delay in wound healing was observed and no adverse events (e.g. sepsis and/or inflammation) were observed during the study. Results summarized in table 5 suggest that dressings according to exemplary embodiments of the invention actually accelerate wound healing relative to previously available standard of care dressings.

Alternatively or additionally, results presented in this example clearly demonstrate that that for the 7 wounds treated with a clotted whole blood dressing according to exemplary embodiments of the invention, the dressing promoted healing.

What is claimed is:

1. A method of dressing a wound of a subject, the method comprising:
   withdrawing a volume of whole blood by sterile withdrawal of venous blood from a subject;
   mixing the volume of whole blood with a coagulation initiator;
   allowing said whole blood to clot at a location physically separated from the wound to obtain a sterile whole-blood clot;
   combining said whole-blood clot with a support matrix to form a sterile wound dressing comprising clotted whole blood and the support matrix; and
   applying said sterile wound dressing onto the wound, and leaving said sterile wound dressing in place for at least two days.

2. The method of claim 1, wherein sterile whole blood is allowed to clot within a receptacle or on a tray.

3. The method of claim 1, wherein the volume of whole blood is spread to a thickness from 1 to 5 mm.

4. The method of claim 1, wherein the coagulation initiator is kaolin.

5. A method for dressing a wound, comprising:
   withdrawing a volume of whole blood by sterile withdrawal of venous blood from a subject;
   mixing the volume of whole blood with a coagulation initiator;
   introducing the volume of whole blood to a receptacle or tray;
   allowing the volume of whole blood to clot to thereby obtain a sterile whole-blood clot;
   transferring said whole blood clot onto the wound,
   applying a support matrix onto the whole blood clot when on said wound, to form a sterile wound dressing comprising clotted whole blood and the support matrix; and
   leaving said sterile wound dressing in place for at least two days.

6. The method of claim 5, wherein the volume of whole blood is spread to a thickness from 1 to 5 mm.

7. The method of claim 5, wherein the coagulation initiator is kaolin.

* * * * *